(12) United States Patent
Stoessel et al.

(10) Patent No.: US 9,425,401 B2
(45) Date of Patent: Aug. 23, 2016

(54) 9,9'-SPIROBIXANTHENE DERIVATIVES FOR ELECTROLUMINESCENT DEVICES

(71) Applicant: MERCK PATENT GMBH, Darmstadt (DE)

(72) Inventors: Philipp Stoessel, Frankfurt am Main (DE); Elvira Montenegro, Weinheim (DE); Arne Buesing, Frankfurt am Main (DE); Teresa Mujica-Fernaud, Darmstadt (DE); Joachim Kaiser, Darmstadt (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 14/387,060

(22) PCT Filed: Feb. 28, 2013

(86) PCT No.: PCT/EP2013/000593
§ 371 (c)(1),
(2) Date: Sep. 22, 2014

(87) PCT Pub. No.: WO2013/139431
PCT Pub. Date: Sep. 26, 2013

(65) Prior Publication Data
US 2015/0045529 A1   Feb. 12, 2015

(30) Foreign Application Priority Data

Mar. 23, 2012 (EP) .................................... 12002073

(51) Int. Cl.
*H01L 51/00* (2006.01)
*C07D 493/10* (2006.01)
*H01L 51/50* (2006.01)

(52) U.S. Cl.
CPC .......... *H01L 51/0035* (2013.01); *C07D 493/10* (2013.01); *H01L 51/0052* (2013.01); *H01L 51/0058* (2013.01); *H01L 51/0061* (2013.01); *H01L 51/0067* (2013.01); *H01L 51/0072* (2013.01); *H01L 51/0073* (2013.01); *H01L 51/5012* (2013.01); *H01L 51/5056* (2013.01); *H01L 51/5072* (2013.01); *H01L 51/5088* (2013.01); *H01L 51/5096* (2013.01)

(58) Field of Classification Search
CPC .......................... H01L 51/00; H01L 51/0035
See application file for complete search history.

(56) References Cited

U.S. PATENT DOCUMENTS 7,318,966 B2   1/2008  Tominaga et al.
8,435,647 B2   5/2013  Pampuch et al.

FOREIGN PATENT DOCUMENTS

| CN | 1397148 A | 2/2003 | |
|---|---|---|---|
| CN | 102227829 A | 10/2011 | |
| EP | 1120840 A2 | 8/2001 | |
| EP | 1341403 A1 | 9/2003 | |
| WO | WO-2006/028977 A2 | 3/2006 | |
| WO | WO 2006028977 A2 * | 3/2006 | |
| WO | WO-2010/061315 A1 | 6/2010 | |
| WO | WO 2010061315 A1 * | 6/2010 | .......... H01L 51/0058 |

OTHER PUBLICATIONS

International Search Report for PCT/EP2013/000593 mailed May 10, 2013.
English translation of Chinese Office Action issued Jul. 14, 2015 for Chinese Application No. 201380016078.6.
English translation of Chinese Office Action issued Mar. 10, 2016 for Chinese Application No. 201380016078.6.

* cited by examiner

*Primary Examiner* — Noble Jarrell
*Assistant Examiner* — John S Kenyon
(74) *Attorney, Agent, or Firm* — Drinker Biddle & Reath LLP

(57) ABSTRACT

The present invention relates to compounds suitable for use in electronic devices, and to electronic devices, especially organic electroluminescent devices, comprising these compounds.

11 Claims, No Drawings

9,9'-SPIROBIXANTHENE DERIVATIVES FOR ELECTROLUMINESCENT DEVICES

CROSS-REFERENCE TO RELATED APPLICATIONS

This application is a national stage application (under 35 U.S.C., §371) of PCT/EP2013/000593, filed Feb. 28, 2013, which claims benefit of European Application No. 12002073.0, filed Mar. 23, 2012, both of which are incorporated herein by reference in their entirety.

The present invention relates to materials for use in electronic devices, in particular in organic electroluminescent devices, and to electronic devices, in particular organic electroluminescent devices, comprising these materials.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence. For quantum-mechanical reasons, an up to four-fold energy and power efficiency is possible using organometallic compounds as phosphorescence emitters. In general, however, there is still a need for improvement in the case of OLEDs, in particular also in the case of OLEDs which exhibit triplet emission (phosphorescence), for example with respect to efficiency, operating voltage and lifetime. In addition, it is desirable that the materials used can be synthesised in high yield and purity.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. For fluorescent OLEDs too, there is still a need for improvement in the case of these materials and for emitters and matrix materials.

In accordance with the prior art, use is made of, inter alia, carbazole derivatives, for example in accordance with WO 2005/039246, US 2005/0069729, JP 2004/288381, EP 1205527, WO 2008/086851 or WO 2010/061315, indolocarbazole derivatives, for example in accordance with WO 2007/063754 or WO 2008/056746, indenocarbazole derivatives, for example in accordance with WO 2010/136109, or dihydroacridine derivatives, for example in accordance with US 2010/0019658, as matrix materials for phosphorescent emitters in organic electroluminescent devices. Further improvements are desirable here, and in relation to the efficiency, the lifetime and the thermal stability of the materials.

In accordance with the prior art, use is furthermore made of arylamine derivatives, in particular triarylamine derivatives and bis(diarylamino)aryl derivatives as hole-injection and hole-transport materials, for example based on spirobifluorenes (for example in accordance with DE 102010045405).

The object of the present invention is the provision of compounds which are suitable for use in a fluorescent or phosphorescent OLED, in particular as matrix material or as hole-injection or hole-transport/electron-blocking material or exciton-blocking material, but also as hole-blocking material, matrix for fluorescent emitters or as fluorescent emitter. A further object of the present invention is to provide further organic semiconductors for organic electroluminescent devices in order thus to provide the person skilled in the art with a greater range of choice of materials for the production of OLEDs.

Surprisingly, it has been found that certain compounds described in greater detail below achieve this object, are highly suitable for use in OLEDs and result in improvements in the organic electroluminescent device. The improvements here relate, in particular, to the lifetime, the efficiency and/or the operating voltage. The present invention therefore relates to these compounds and to electronic devices, in particular organic electroluminescent devices, which comprise compounds of this type.

The present invention relates to a compound of the formula (1),

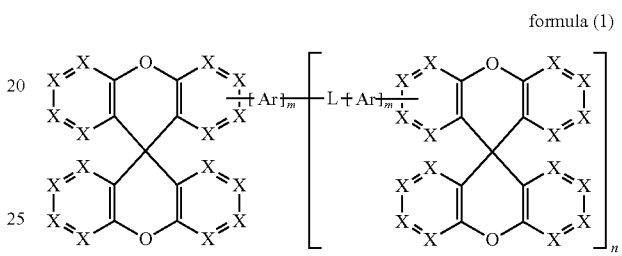

formula (1)

where the following applies to the symbols and indices used:

X is on each occurrence, identically or differently, $CR^1$ or N; or two adjacent X stand for S, O or $NR^1$, so that a five-membered ring forms; or two adjacent X stand for a group of the following formula (2), (3) or (4),

formula (2)

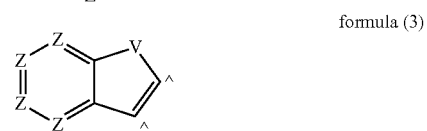

formula (3)

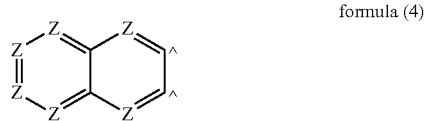

formula (4)

where ^ indicates the corresponding adjacent groups X in the formula (1);

X here stands for C if a group Ar or L is bonded to this group X;

V is on each occurrence, identically or differently, $C(R^1)_2$, $NR^1$, O or S;

Z is on each occurrence, identically or differently, $CR^1$ or N;

Ar is on each occurrence, identically or differently, an aromatic or heteroaromatic ring system having 5 to 40 aromatic ring atoms, which may be substituted by one or more radicals $R^2$; the group Ar and the adjacent group X, which in this case stands for C, may also be bridged to one another here by a single bond or a divalent group selected from $C(R^2)_2$, $NR^2$, O or S;

L is on each occurrence, identically or differently, a single bond or a divalent group;

$R^1$, $R^2$ is selected on each occurrence, identically or differently, from the group consisting of H, D, F, Cl, Br, I, CN, $NO_2$, $N(Ar^1)_2$, $N(R^3)_2$, $C(=O)Ar^1$, $C(=O)R^3$, $P(=O)(Ar^1)_2$, $P(Ar^1)_2$, $B(Ar^1)_2$, $Si(Ar^1)_3$, $Si(R^3)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $R^3C=CR^3$, $C\equiv C$, $Si(R^3)_2$, $C=O$, $C=S$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^3$, an aryloxy or heteroaryloxy group having 5 to 60 aromatic ring atoms, which may be substituted by one or more radicals $R^3$, where two or more adjacent substituents $R^1$ or $R^2$ may optionally form a monocyclic or polycyclic, aliphatic, aromatic or heteroaromatic ring system, which may be substituted by one or more radicals $R^3$;

$Ar^1$ is on each occurrence, identically or differently, an aromatic or heteroaromatic ring system having 5-30 aromatic ring atoms, which may be substituted by one or more non-aromatic radicals $R^3$; two radicals $Ar^1$ here which are bonded to the same N atom or P atom may also be bridged to one another by a single bond or a bridge selected from $N(R^3)$, $C(R^3)_2$, O or S;

$R^3$ is selected on each occurrence, identically or differently, from the group consisting of H, D, F, Cl, Br, I, CN, $NO_2$, $N(R^4)_2$, $C(=O)R^4$, $P(=O)(R^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^4$, where one or more non-adjacent $CH_2$ groups may be replaced by $R^4C=CR^4$, $C\equiv C$, $Si(R^4)_2$, $C=O$, $C=S$, $C=NR^4$, $P(=O)(R^4)$, SO, $SO_2$, $NR^4$, O, S or $CONR^4$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^4$, an aryloxy or heteroaryloxy group having 5 to 60 aromatic ring atoms, which may be substituted by one or more radicals $R^4$, or a combination of these systems, where two or more adjacent substituents $R^3$ may optionally form a monocyclic or polycyclic, aliphatic ring system, which may be substituted by one or more radicals $R^4$;

$R^4$ is selected on each occurrence, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^4$ may form a mono- or polycyclic, aliphatic ring system with one another;

m is on each occurrence, identically or differently, 0 or 1;

n is 0, 1, 2, 3, 4 or 5;

with the proviso that that for n=0, at least one substituent $R^1$ is present which is selected from the group consisting of CN, $N(Ar^1)_2$, $C(=O)Ar^1$, $P(=O)(Ar^1)_2$, $P(Ar^1)_2$, $B(Ar^1)_2$, $Si(Ar^1)_3$, $Si(R^3)_3$ or an aromatic or heteroaromatic ring system having 5 to 60 aromatic ring atoms, which may in each case be substituted by one or more radicals $R_3$;

compounds of the formula (1) in which n=0 and four substituents $R^1$ stand, identically or differently, for an optionally substituted carbazole or diphenylamine, which is in each case bonded to the skeleton via the nitrogen atom, are excluded from the invention.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by a short alkyl group.

For the purposes of the present invention, an aliphatic hydrocarbon radical or an alkyl group or an alkenyl or alkynyl group, which may contain 1 to 40 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethyl-thio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent CH$_2$ groups may be replaced by the above-mentioned groups; furthermore, one or more H atoms may also be replaced by D, F, Cl, Br, I, CN or NO$_2$, preferably F, Cl or CN, further preferably F or CN, particularly preferably CN.

An aromatic or heteroaromatic ring system having 5-60 aromatic ring atoms, which may also in each case be substituted by the above-mentioned radicals R$^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, pyrene, chrysene, perylene, fluoranthene, naphthacene, penta-cene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimi-dazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzo-pyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems.

In an embodiment of the invention, compounds of the formula (1) in which R$^1$ stands, identically or differently, for carbazole or for a substituted carbazole, which is in each case bonded to the skeleton via the nitrogen atom, or for diphenylamine or for a substituted diphenylamine are excluded from the invention.

In a preferred embodiment of the invention, X stands, identically or differently on each occurrence, for CR$^1$ or N, where a maximum of one group X per ring stands for N; or two adjacent groups X stand for a group of the formula (2), (3) or (4), in particular formula (3), where Z stands, identically or differently on each occurrence, for CR$^1$ and V stands, identically or differently on each occurrence, for NR$^1$ or C(R$^1$)$_2$. Furthermore preferably, adjacent radicals R$^1$ which are present on X do not form a ring with one another.

Particularly preferably, X stands, identically or differently on each occurrence, for CR$^1$.

Preference is furthermore given to compounds of the following formulae (1a), (1b), (1c) and (1d),

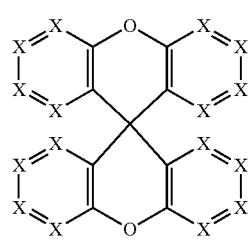

formula (1a)

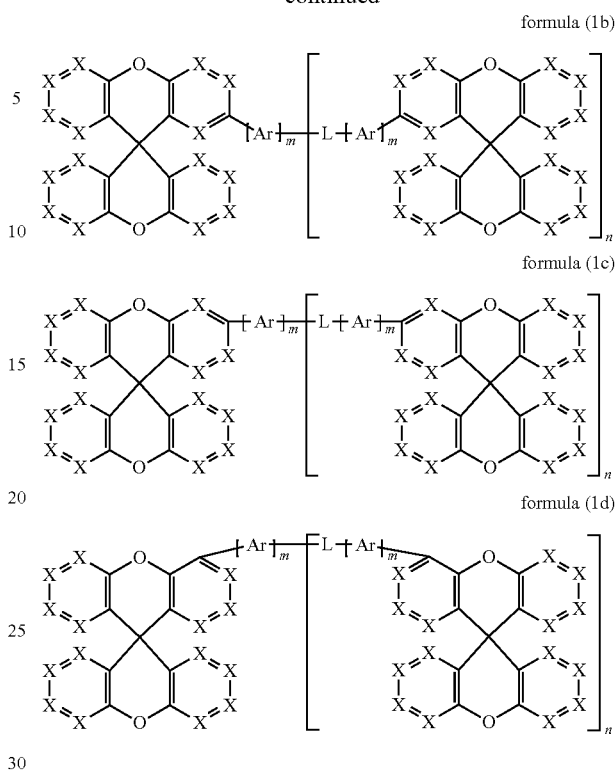

formula (1b)

formula (1c)

formula (1d)

where the symbols and indices used have the meanings given above.

Particular preference is given to compounds of the above-mentioned formula (1) where n=0, i.e. compounds of the above-mentioned formula (1a).

Preference is furthermore given to compounds where n=1 and m=0, in particular compounds of the following formulae (1e), (1f) and (1g), and compounds where n=1, one m=0 and the other m=1 and L=single bond, in particular compounds of the following formulae (1h), (1i) and (1j),

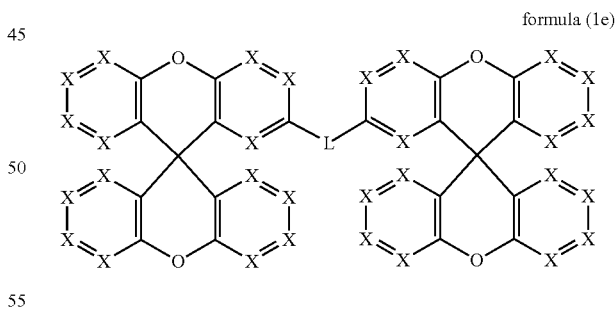

formula (1e)

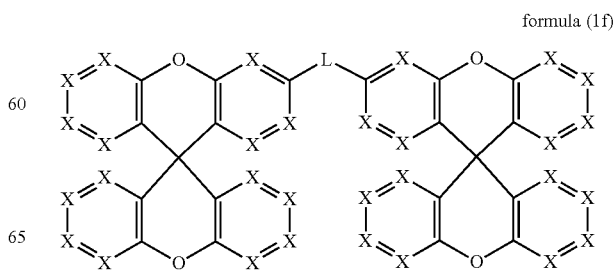

formula (1f)

formula (1g)

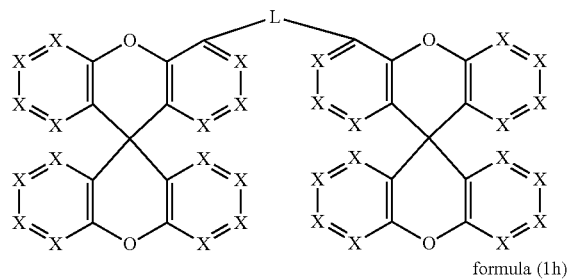

formula (1h)

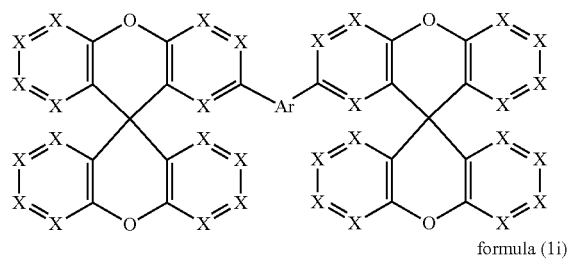

formula (1i)

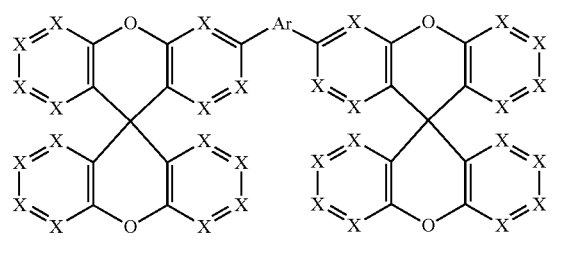

formula (1j)

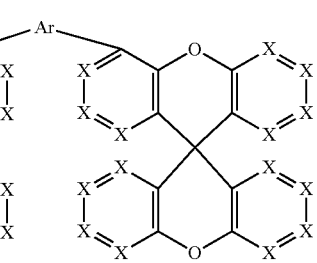

where the symbols us formula (1d) the meanings given above.

In a preferred embodiment of the invention, the group L stands, identically or differently on each occurrence, for a straight-chain alkylene or alkylidene group having 1 to 10 C atoms or a branched or cyclic alkylene or alkylidene group having 3 to 40 C atoms or an alkenylene or alkynylene group having 2 to 40 C atoms, which may be substituted by in each case one or more radicals $R^3$, where one or more non-adjacent $CH_2$ groups may be replaced by $-R^3C=CR^3-$, $-C\equiv C-$, $Si(R^3)_2$, $C=O$, $-O-$, $-S-$ or $-CONR^3-$ and where one or more H atoms may be replaced by D, F, Cl, Br, I, CN or $NO_2$, or $P(R^3)$, $P(=O)(R^3)$, $N(Ar)$; or L is a single bond.

Particularly preferred embodiments of the compounds of the formula (1) or (1a) are the compounds of the following formula (5) and particularly preferred embodiments of the compounds of the formula (1b), (1c) and (1d) are the compounds of the following formulae (6), (7) and (8), formula (5)

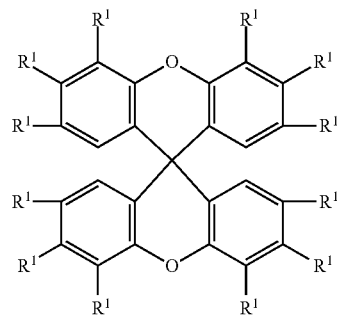

formula (6)

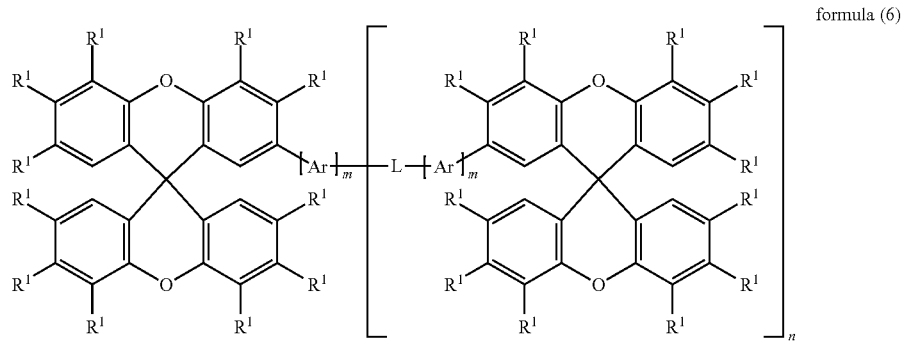

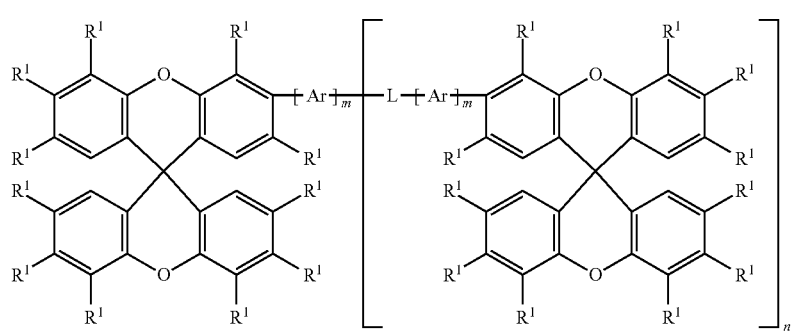
formula (7)
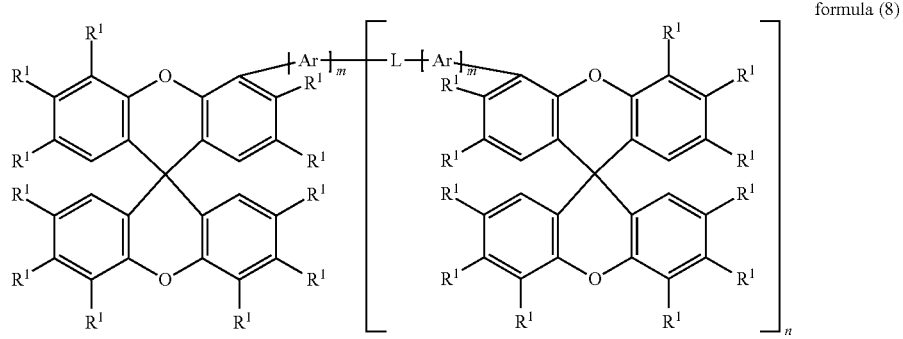
formula (8)
where the symbols and indices used have the meanings given above.
Furthermore, groups of the formula (2), (3) or (4) can be condensed on, as depicted below by way of example by the formulae (9), (10), (11) and (12) with condensed-on groups of the formula (3),
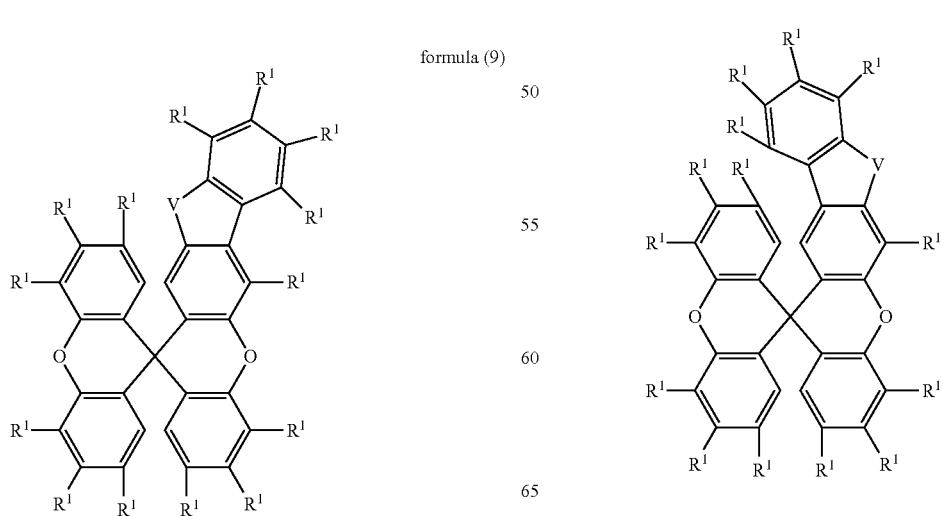
formula (9)
formula (10)

formula (11)

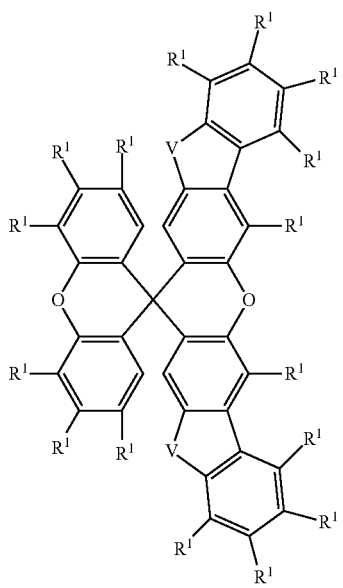

formula (12)

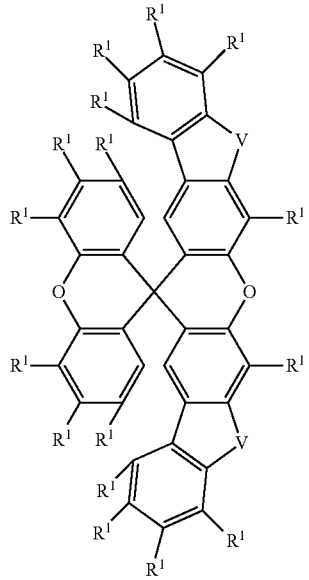

where the symbols and indices used have the meanings given above. It may be preferred here, for V=C(R¹)₂, for the two radicals R¹ to form a ring with one another and thus to form a spiro system.

In a preferred embodiment of the invention, a maximum of two substituents R¹ are not equal to H or D.

Particularly preferred embodiments of the structures of the formula (5) are the structures of the formulae (5a) to (5u), formula (5a)

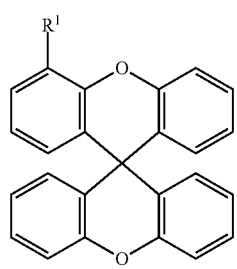

formula (5b)

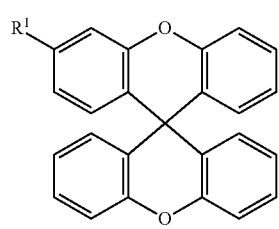

formula (5c)

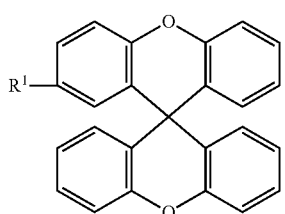

formula (5d)

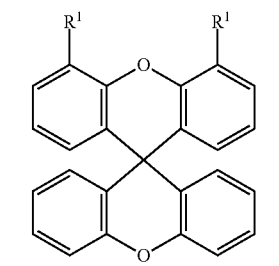

formula (5e)

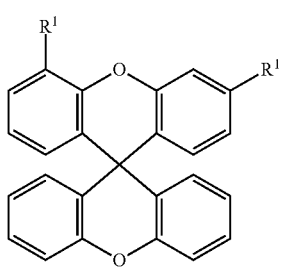

formula (5f)

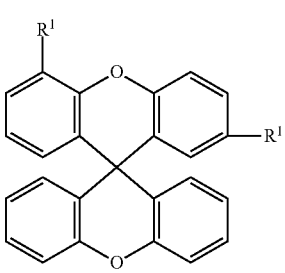

formula (5g)

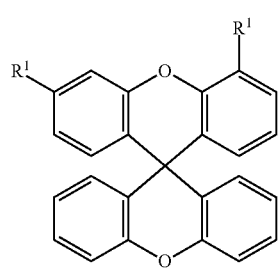

formula (5h)
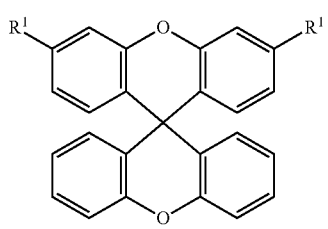
formula (5i)
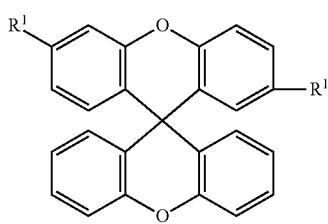
formula (5j)
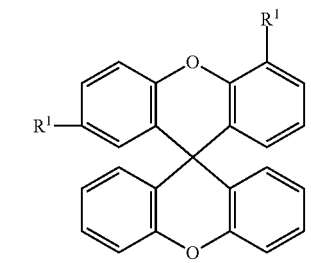
formula (5k)
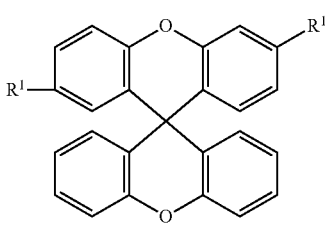
formula (5l)
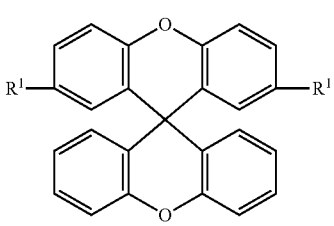
formula (5m)
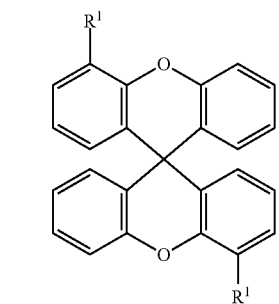
formula (5n)
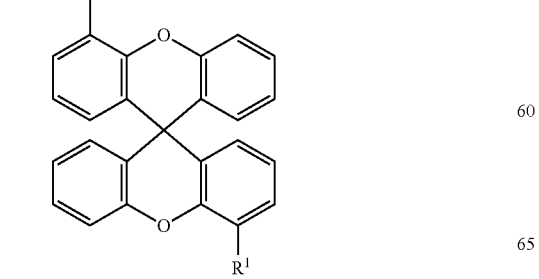
formula (5o)
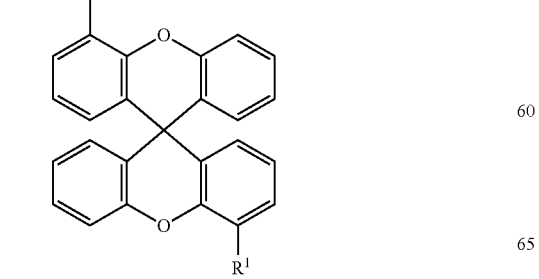
formula (5p)
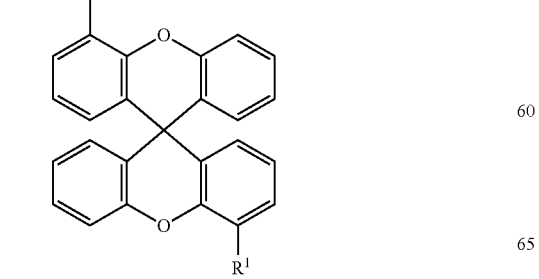
formula (5q)
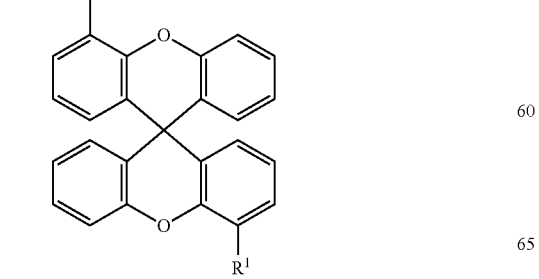
formula (5r)
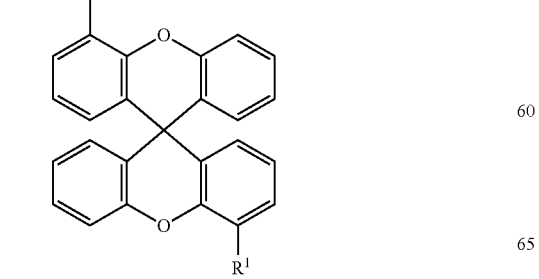
formula (5s)
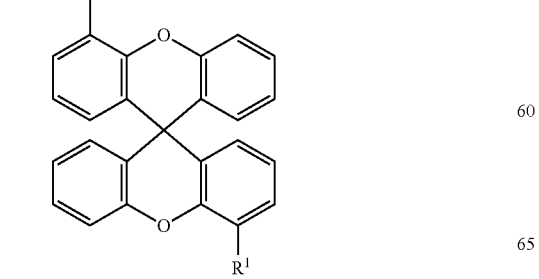

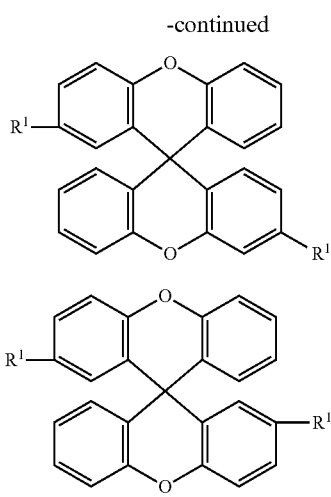

formula (5t)

formula (5u)

where the symbols and indices used have the meanings given above.

Particularly preferred structures are the structures of the above-mentioned formulae (5a), (5b), (5c), (5d), (5h), (5l), (5m) and (5u).

Particular preference is also given to structures of the above-mentioned formulae which contain two groups $R^1$, where one group $R^1$ is a hole-transporting unit and the other group $R^1$ is an electron-transporting unit. The hole-transporting unit $R^1$ here is, in particular, an optionally substituted carbazole group or a derivative thereof or an optionally substituted diarylamino group or triarylamino group. The electron-transporting unit $R^1$ is, in particular, an optionally substituted electron-deficient heteroaryl group, in particular an optionally substituted triazine or pyrimidine, an aromatic ketone —C(=O)Ar$^1$ or an aromatic phosphine oxide —P(=O)(Ar$^1$)$_2$.

In a preferred embodiment of the invention, $R^1$ and $R^2$ in the above-mentioned formulae are selected, identically or differently on each occurrence, from the group consisting of H, D, F, Cl, Br, CN, N(Ar$^1$)$_2$, C(=O)Ar$^1$, P(=O)(Ar$^1$)$_2$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which may be substituted by one or more radicals $R^3$, where one or more non-adjacent CH$_2$ groups may be replaced by O and where one or more H atoms may be replaced by D or F, an aromatic or heteroaromatic ring system having 5 to 30 aromatic ring atoms, which may in each case be substituted by one or more radicals $R^3$.

In a particularly preferred embodiment of the invention, $R^1$ and $R^2$ in the above-mentioned formulae are selected, identically or differently on each occurrence, from the group consisting of H, D, F, Cl, Br, CN, a straight-chain alkyl group having 1 to 5 C atoms or a branched or cyclic alkyl group having 3 to 10 C atoms, where one or more H atoms may be replaced by D or F, an aromatic or heteroaromatic ring system having 5 to 18 aromatic ring atoms, which may in each case be substituted by one or more radicals $R^3$.

In compounds where n=0, at least one group $R^1$ stands, as described above, for a substituent which is selected from the group consisting of CN, N(Ar$^1$)$_2$, C(=O)Ar$^1$, P(=O)(Ar$^1$)$_2$, P(Ar$^1$)$_2$, B(Ar$^1$)$_2$, Si(Ar$^1$)$_3$, Si(R$^3$)$_3$, an aromatic or heteroaromatic ring system having 5 to 60 aromatic ring atoms, which may in each case be substituted by one or more radicals $R^3$. This substituent is preferably selected from the group consisting of N(Ar$^1$)$_2$, C(=O)Ar$^1$, P(=O)(Ar$^1$)$_2$ or an aromatic or heteroaromatic ring system having 5 to 40, particularly preferably having 5 to 18 aromatic ring atoms, which may in each case be substituted by one or more radicals $R^3$.

For compounds which are processed by vacuum evaporation, the alkyl groups preferably have not more than five C atoms, particularly preferably not more than 4 C atoms, very particularly preferably not more than 1 C atom. For compounds which are processed from solution, compounds which are substituted by alkyl groups, in particular branched alkyl groups, having up to 10 C atoms or which are substituted by oligoarylene groups, for example ortho-, meta-, para- or branched terphenyl or quaterphenyl groups, are also suitable.

Preferred groups Ar are selected from aromatic or heteroaromatic ring systems having 5 to 24 aromatic ring atoms, which may in each case be substituted by one or more radicals $R^3$. Particularly preferred groups Ar are selected from benzene, ortho-, meta- or para-biphenyl, ortho-, meta-, para- or branched terphenyl, ortho-, meta- para- or branched quaterphenyl, 1- or 2-naphthyl, pyrrole, furan, thiophene, indole, benzofuran, benzothiophene, carbazole, dibenzofuran, dibenzothiophene, pyridine, pyrimidine, pyrazine, pyridazine, triazine, anthracene, phenanthrene, pyrene, benzanthracene or combinations of two or three of these groups, each of which may be substituted by one or more radicals $R^3$.

If $R^1$ or $R^2$ stand for an aromatic or heteroaromatic ring system, this is preferably selected, identically or differently on each occurrence, from the same groups as indicated above as preferred groups for Ar.

If the compounds of the formula (1) or the preferred embodiments are used as electron-transport material, it is preferred for at least one of the radicals $R^1$, $R^2$ and/or Ar to stand for an electron-deficient heteroaromatic ring system or —C(=O)Ar$^1$ or —P(=O)(Ar$^1$)$_2$. Electron-deficient heteroaromatic ring systems are in accordance with the invention five-membered heteroaromatic ring systems having at least two heteroatoms or six-membered heteroaromatic ring systems, onto which one or more aromatic or heteroaromatic groups may in each case also be condensed, for example substituted or unsubstituted imidazoles, pyrazoles, thiazoles, oxazoles, oxadiazoles, triazoles, pyridines, pyrazines, pyrimidines, pyridazines, triazines, benzimidazoles, etc., in particular those as shown below.

If the compound according to the invention is employed as matrix material for a phosphorescent emitter or as electron-transport material, at least one substituent $R^1$ and/or $R^2$ or a monovalent group Ar is preferably an electron-deficient group, in particular selected from structures of the following formulae (13) to (16) for $R^1$ or $R^2$ or the formulae (17), (18) or (19) for Ar,

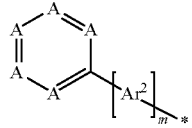

formula (13)

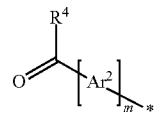

formula (14)

formula (15)

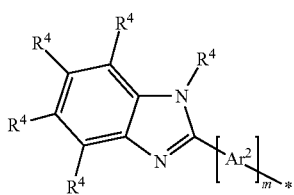

formula (16)

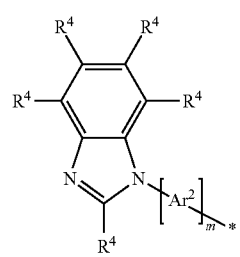

and/or at least one divalent or trivalent group Ar preferably stands for a group of the following formulae (17) to (19), formula (17)

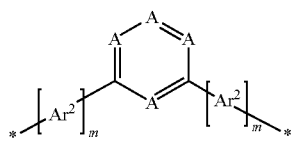

formula (18)

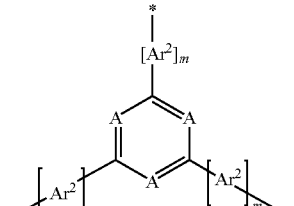

formula (19)

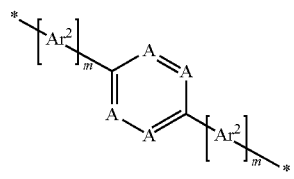

where $R^4$ and m have the meaning given above, * indicates the position of the bonding of the group of the formula (13) to (19) and furthermore:

A is on each occurrence, identically or differently, $CR^4$ or N, with the proviso that one, two or three groups A stand for N;

$Ar^2$ is, identically or differently on each occurrence, a divalent aromatic or heteroaromatic ring system having 5 to 16 C atoms, which may be substituted by one or more radicals $R^4$.

In a particularly preferred embodiment of the invention, at least one substituent $R^1$, $R^2$ or Ar stands for a group of the above-mentioned formula (13), and/or at least one group Ar stands for a group of the above-mentioned formulae (17) to (19), where in each case two or three symbols A stand for N and the other symbols A stand for $CR^4$. Particularly preferred groups $R^1$, $R^2$ or Ar are therefore the groups of the following formulae (20) to (26), and particularly preferred groups Ar are the groups of the following formulae (27) to (34), formula (20)

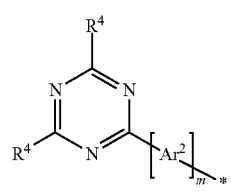

formula (21)

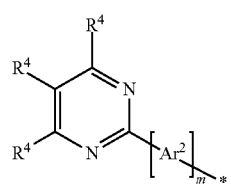

formula (22)

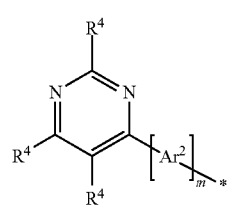

formula (23)

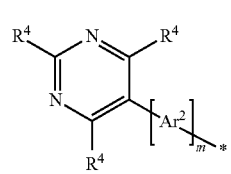

formula (24)

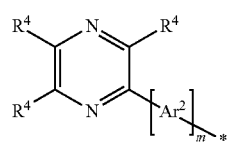

formula (25)

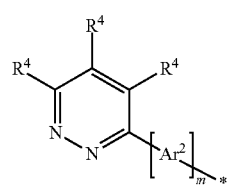

formula (26)

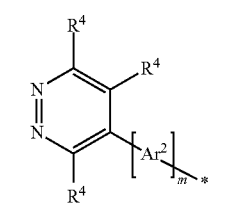

formula (27)

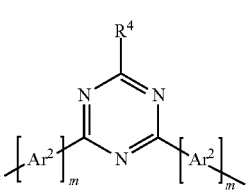

formula (28)

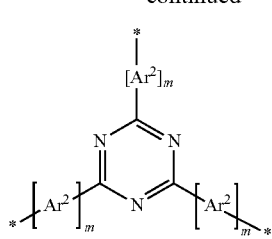

formula (29)

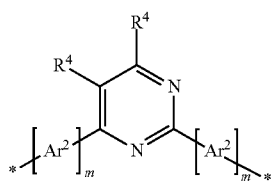

formula (30)

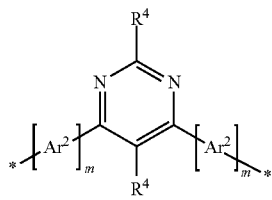

formula (31)

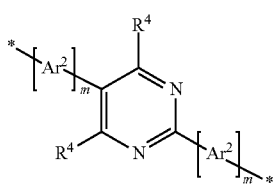

formula (32)

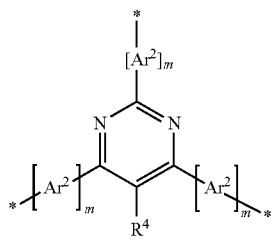

formula (33)

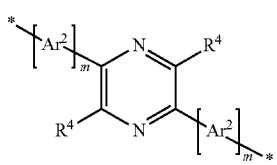

formula (34)

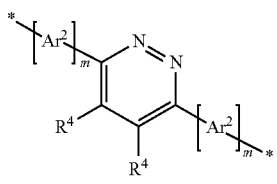

where the symbols and indices used have the meanings given above.

If $R^1$, $R^2$ or Ar stands for a group of the formula (20), $R^4$ in this group then preferably stands for an aromatic or heteroaromatic ring system having 5 to 24 aromatic ring atoms, which may be substituted by one or more radicals $R^5$, in particular for phenyl, ortho-, meta- or para-biphenyl, ortho-, meta-, para- or branched terphenyl or ortho-, meta-, para- or branched quaterphenyl.

If $R^1$, $R^2$ or Ar stands for a group of the formula (21) to (34), $R^4$ in these groups then preferably stands, identically or differently on each occurrence, for H, D or an aromatic or heteroaromatic ring system having 5 to 24 aromatic ring atoms, which may be substituted by one or more radicals $R^5$, in particular for H or phenyl, ortho-, meta- or para-biphenyl, ortho-, meta-, para- or branched terphenyl or ortho-, meta-, para- or branched quaterphenyl.

If the compound according to the invention is employed as matrix material for a phosphorescent emitter, as hole-transport material or as electron- or exciton-blocking material, at least one substituent $R^1$, $R^2$ or Ar is preferably selected from the group consisting of triarylamine derivatives, carbazole derivatives, indenocarbazole derivatives, indolocarbazole derivatives, azacarbazole derivatives, indole derivatives, furan derivatives, benzofuran derivatives, dibenzofuran derivatives, thiophene derivatives, benzothiophene derivatives or dibenzothiophene derivatives, each of which may be substituted by one or more radicals $R^3$, or at least one substituent $R^1$ or $R^2$ stands for —N(Ar$^1$)$_2$. These groups are preferably selected from the groups of the following formulae (35) to (49), formula (35)

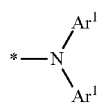

formula (36)

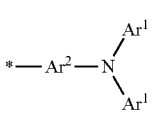

formula (37)

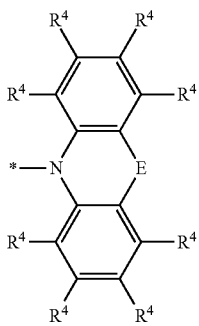

formula (38)

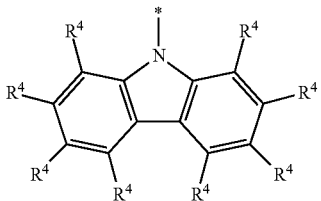

formula (39)

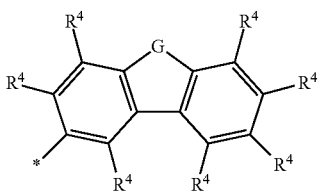

Formel (40)

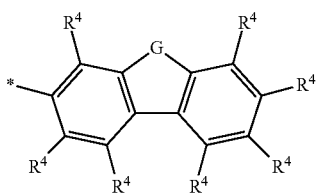

formula (41)

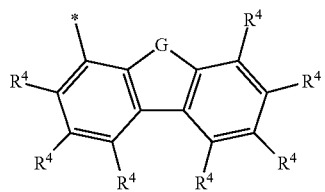

formula (42)

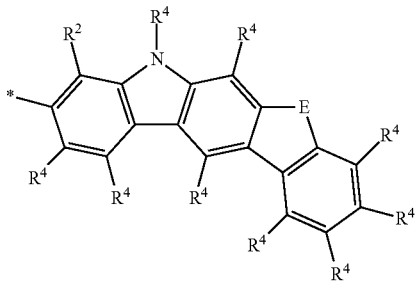

formula (43)

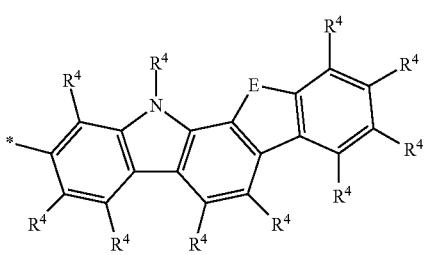

formula (44)

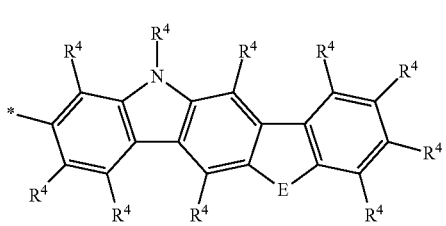

formula (45)

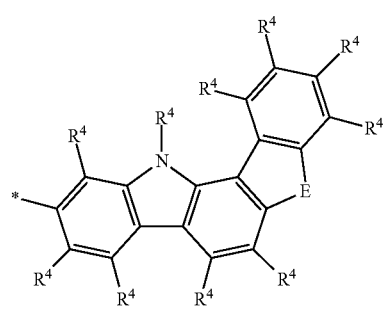

formula (46)

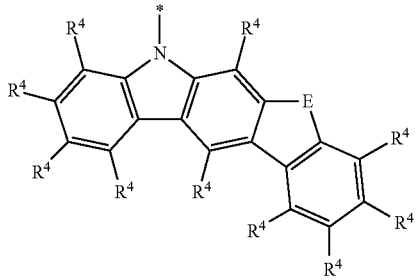

formula (47)

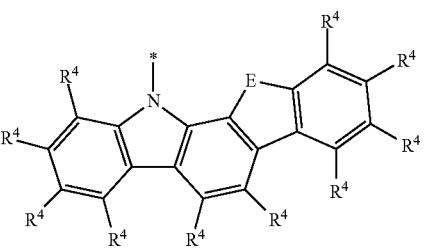

formula (48)

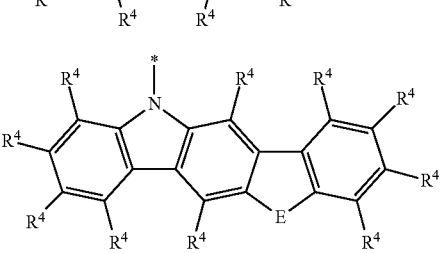

formula (49)

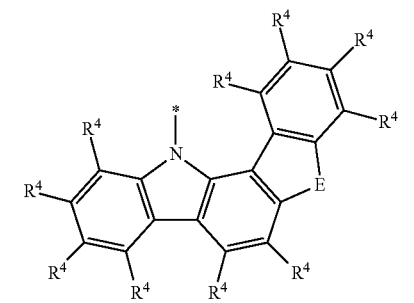

where the symbols used have the meanings given above and furthermore:

E is selected from the group consisting of $C(R^3)_2$, $NR^3$, O or S;

G is selected from the group consisting of $NR^3$, O or S.

In a further preferred embodiment of the invention, the symbols $R^1$ and $R^2$ in the compounds according to the invention which do not stand for a group of the above-mentioned formulae (13) to (49) stand for H or D.

The preferred embodiments mentioned above can be combined with one another as desired. In a particularly preferred embodiment of the invention, the above-mentioned preferences occur simultaneously.

If the compounds of the formula (1) or the preferred embodiments are used as matrix material for a phosphorescent emitter, it is preferred for the compound to contain no condensed aryl or heteroaryl groups in which more than two six-membered rings are condensed directly onto one another. In particular, it is preferred for the radicals $R^1$, $R^2$ and Ar to contain no condensed aryl or heteroaryl group in which two or more six-membered rings are condensed directly onto one another and for two adjacent groups X not to stand for a group of the formula (2) or (4). The compound of the formula (1) particularly preferably contains absolutely no condensed aryl or heteroaryl groups in which six-membered rings are condensed directly onto one another.

If the compounds of the formula (1) or the preferred embodiments are used as matrix material for a fluorescent emitter or as fluorescent emitter, it is preferred for at least one of the radicals $R^1$ and/or $R^2$ to contain a group which is selected from naphthalene, anthracene, phenanthrene, pyrene and/or benzanthracene, each of which may also be substituted by the above-mentioned groups, and/or for two adjacent groups X at least on one of the aromatic rings to stand for a group of the formula (2) or (4).

Examples of preferred compounds in accordance with the embodiments shown above are the compounds of the following structures 1 to 109.

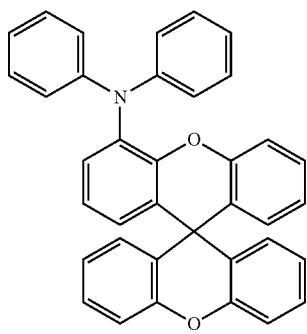

1

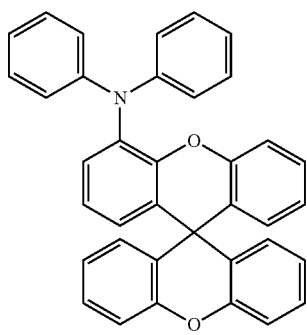

2

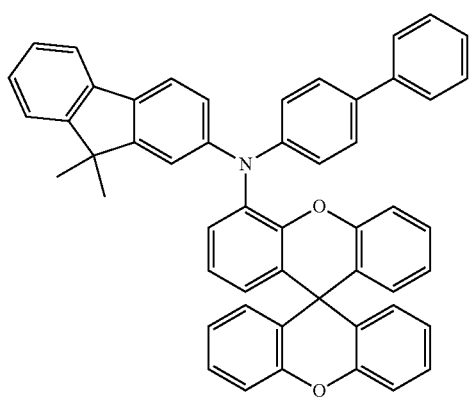

3

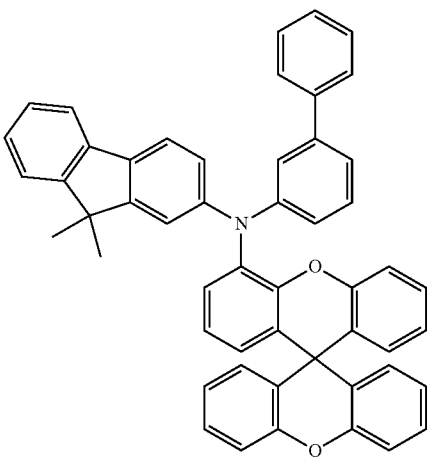

4

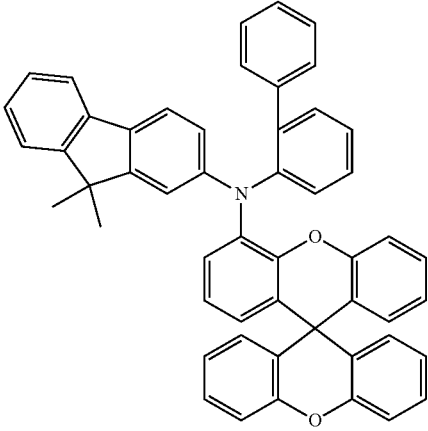

5

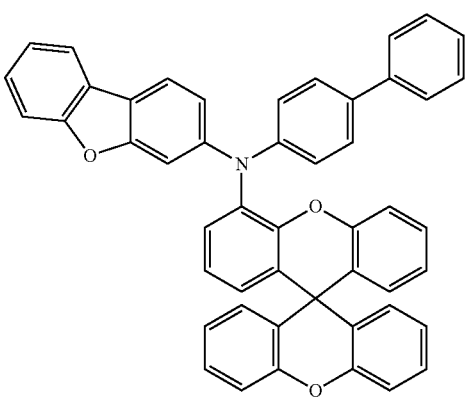

6

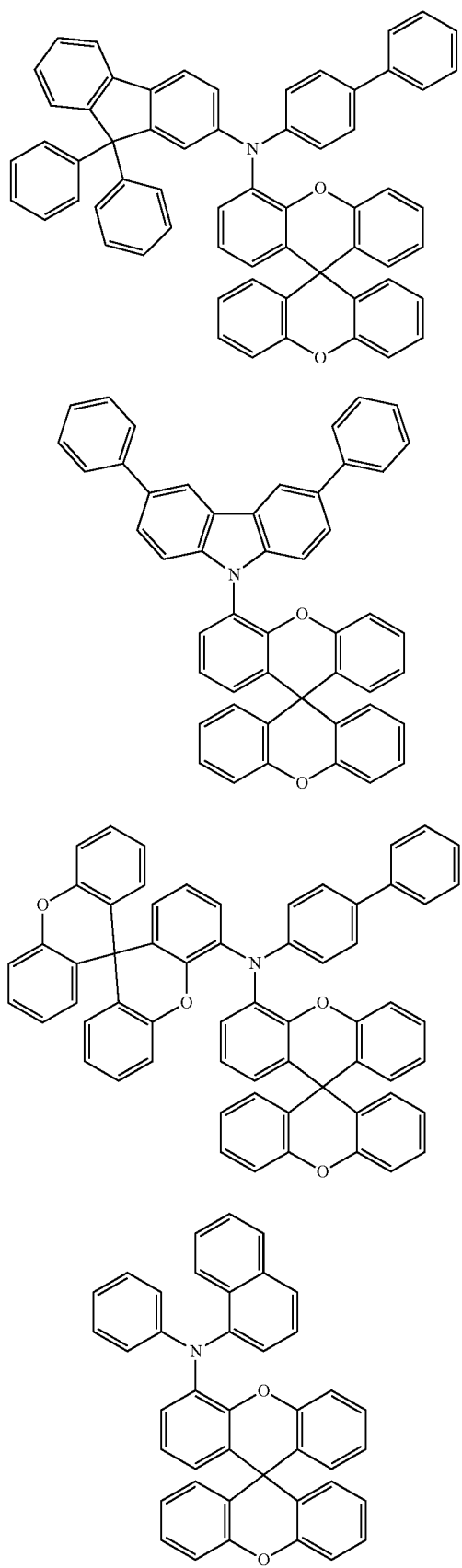
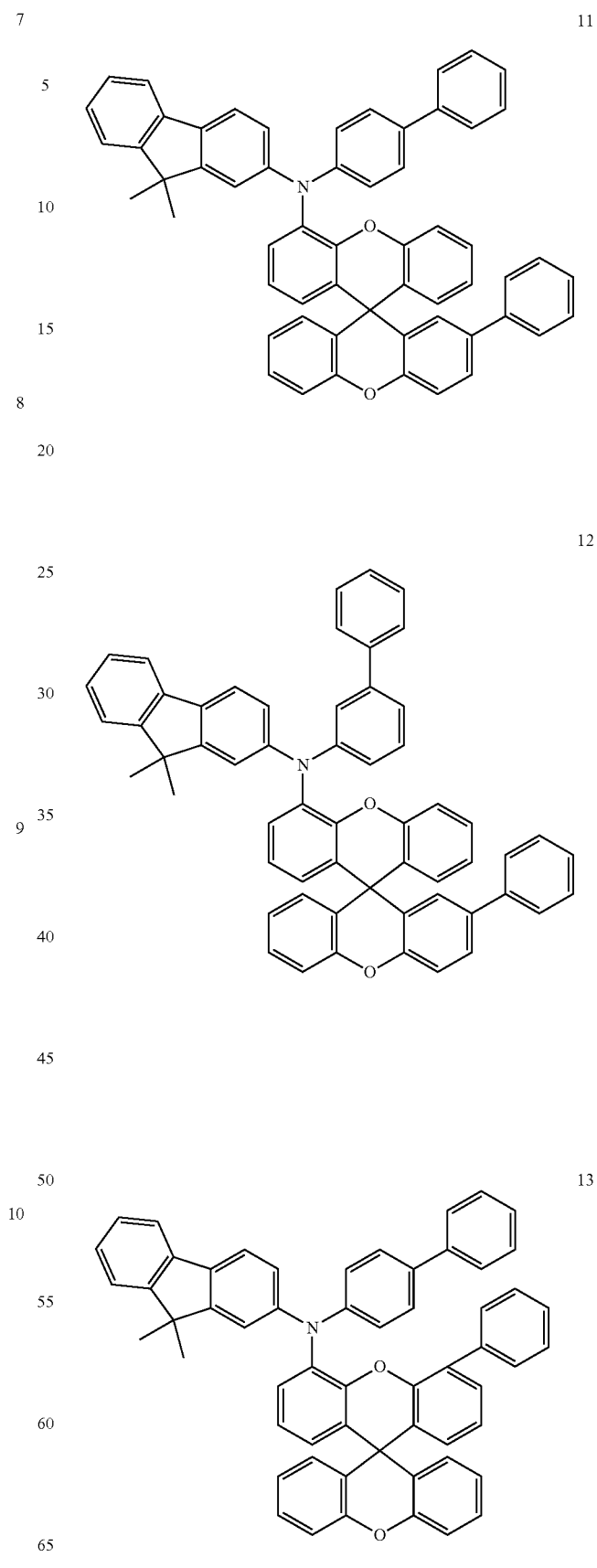

14
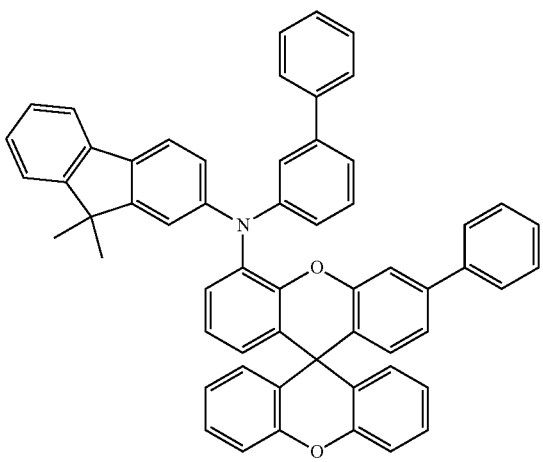
15
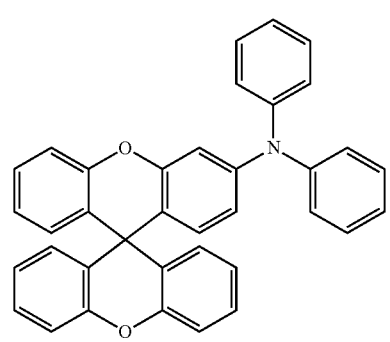
16
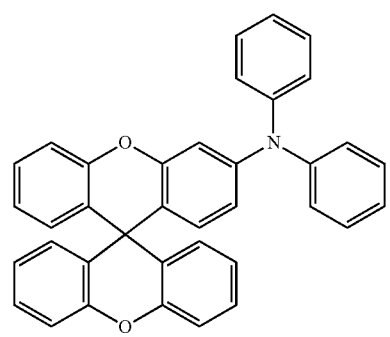
17
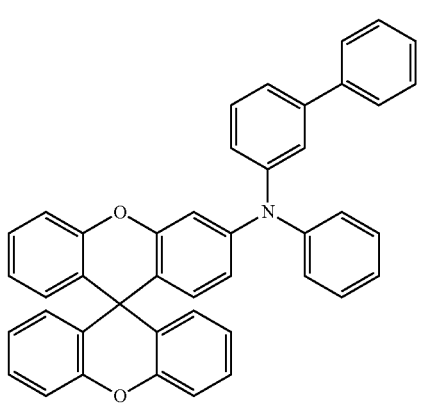
18
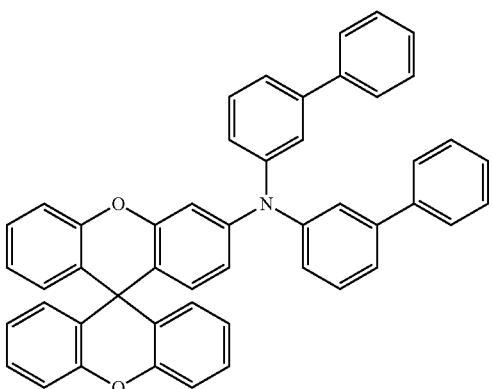
19
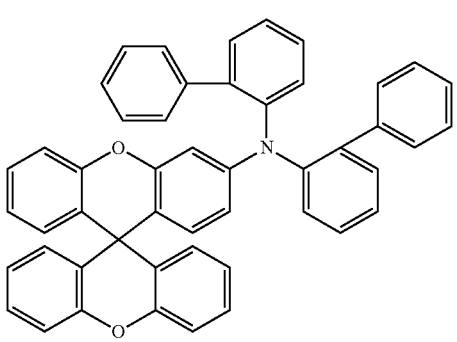
20
21

22
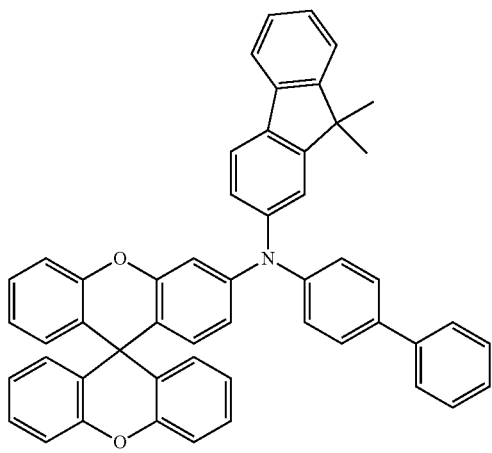
23
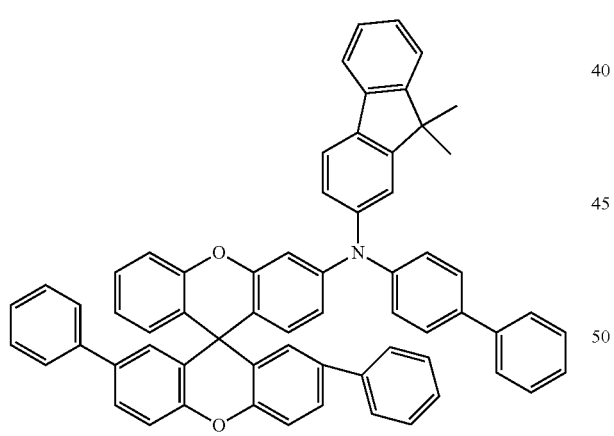
24
25
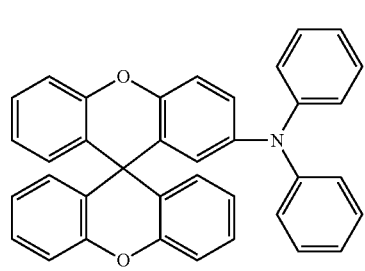
26
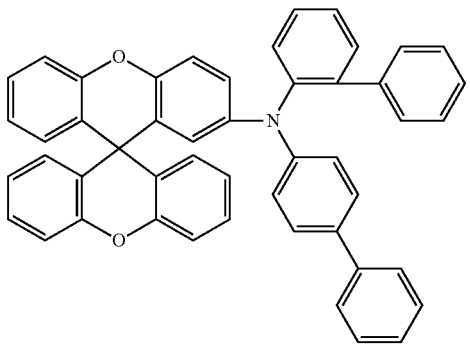
27
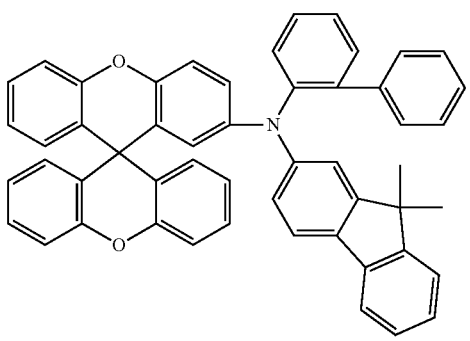
28
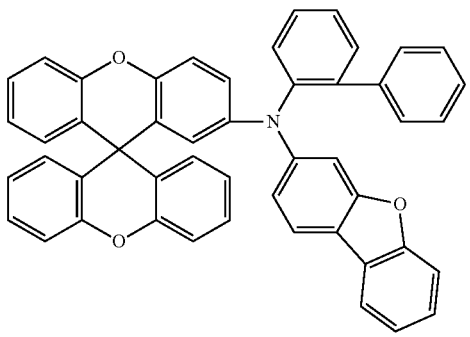
29
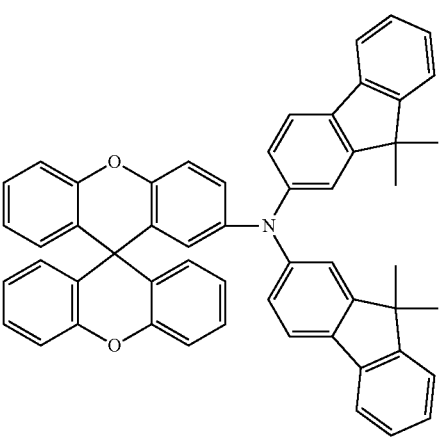

31
-continued
30
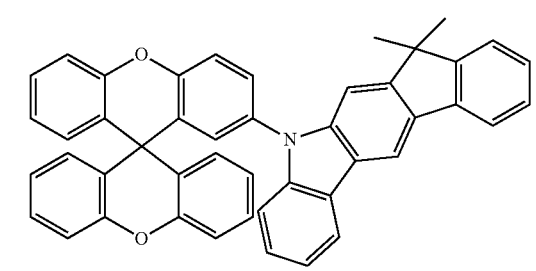
31
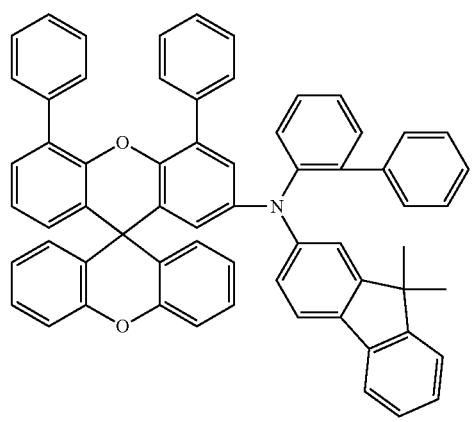
32
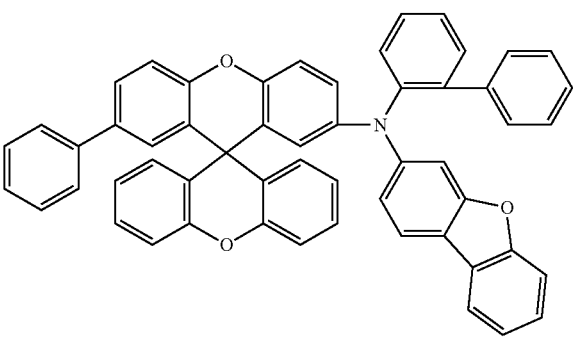
33
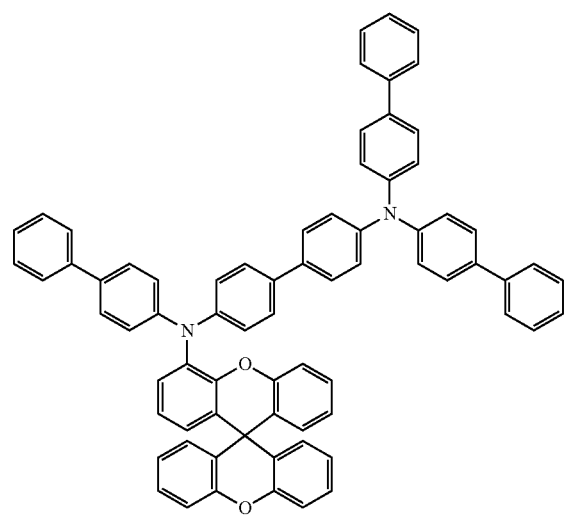
32
-continued
34
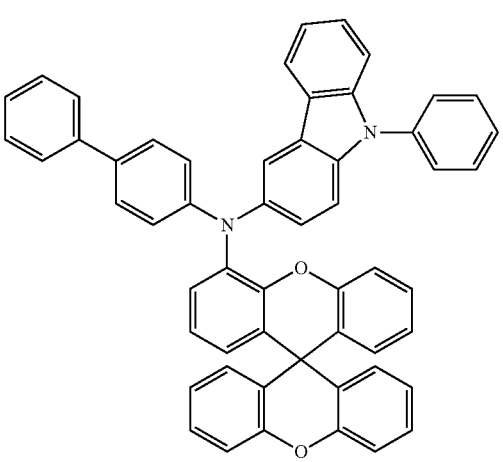
35
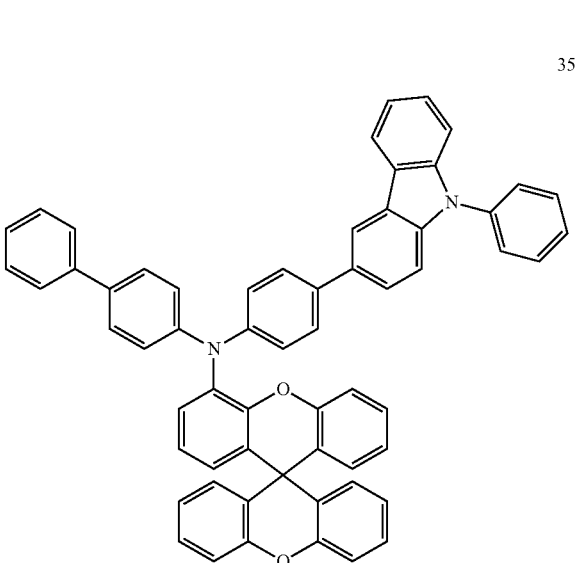
36
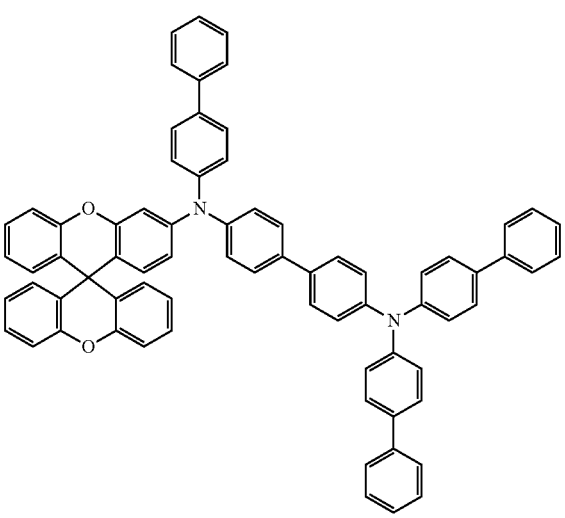

37
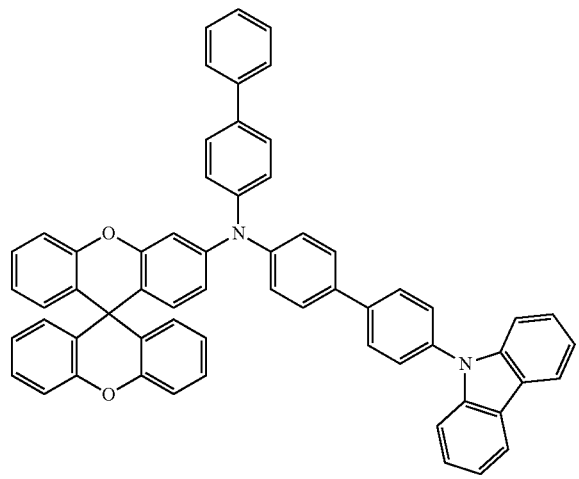
38
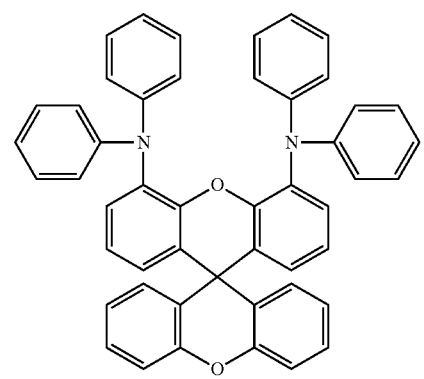
39
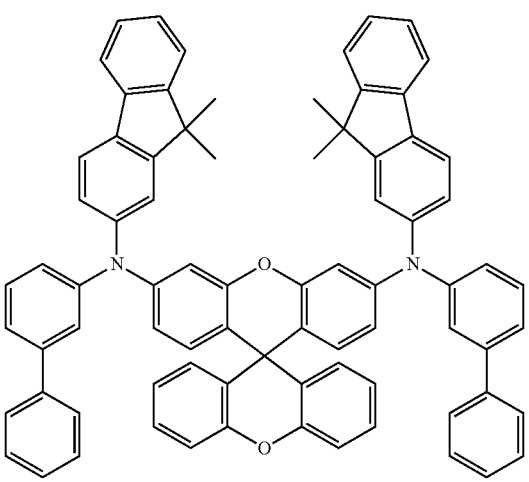
40
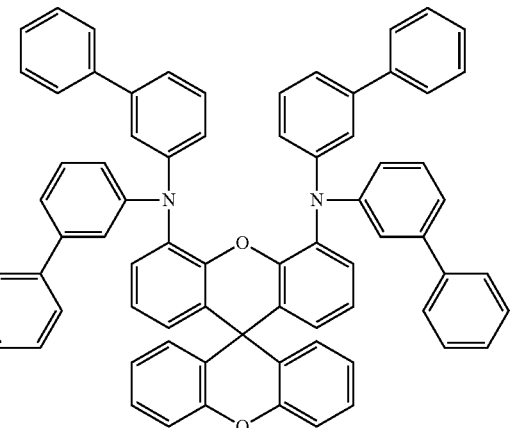
41
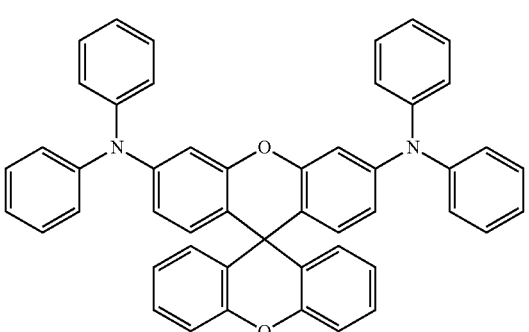
42
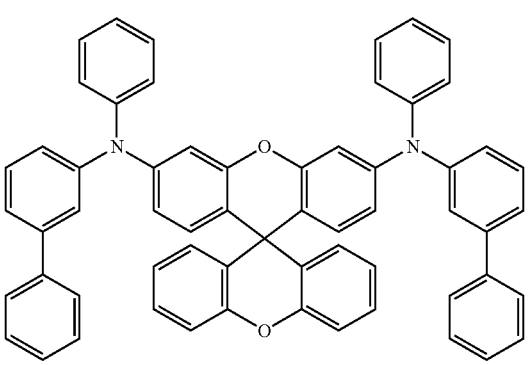
43
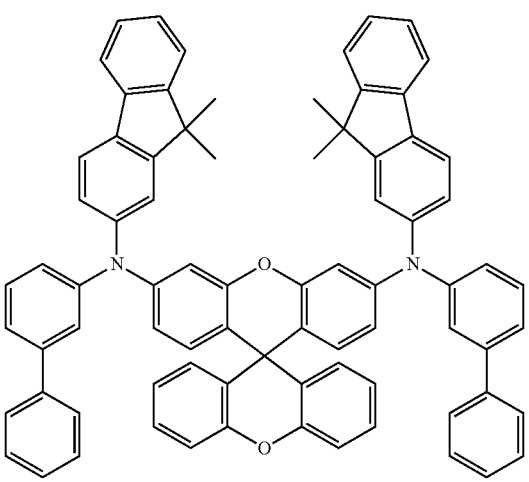

-continued
44
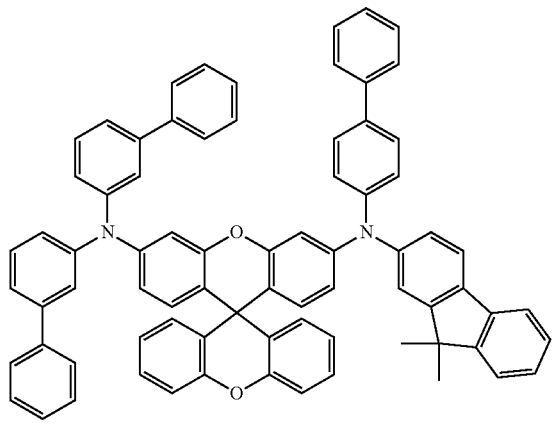
45
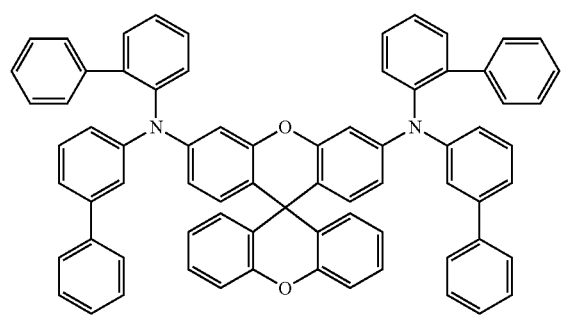
46
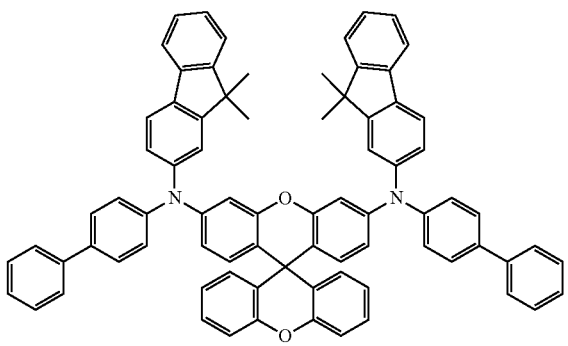
47
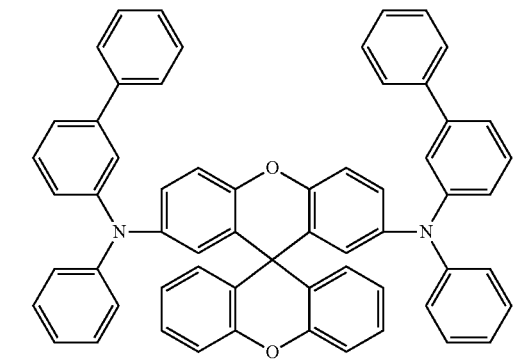
-continued
48
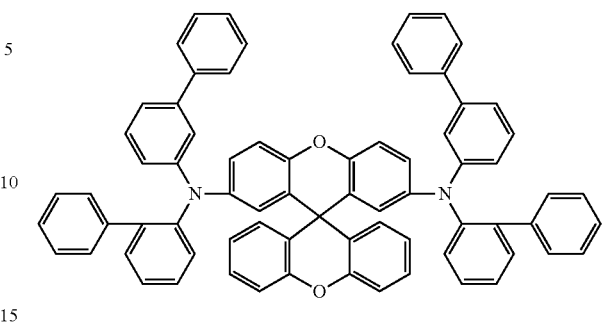
49
50
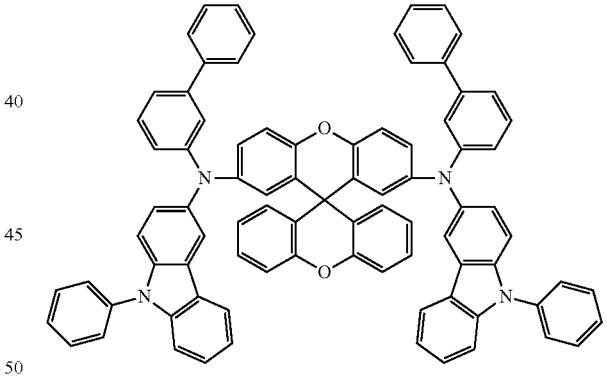
51

-continued
52
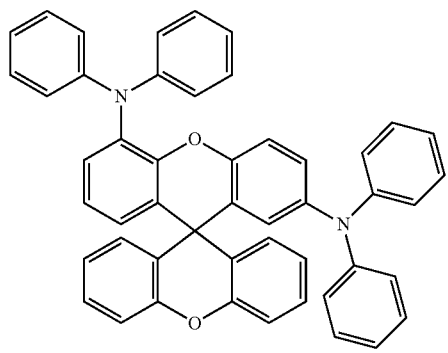
53
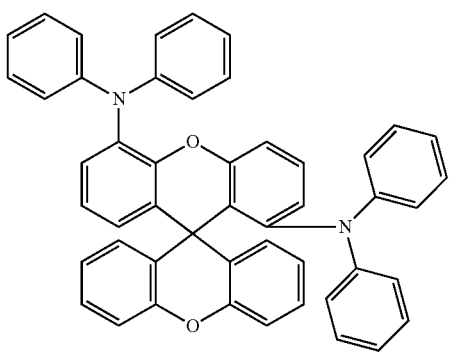
54
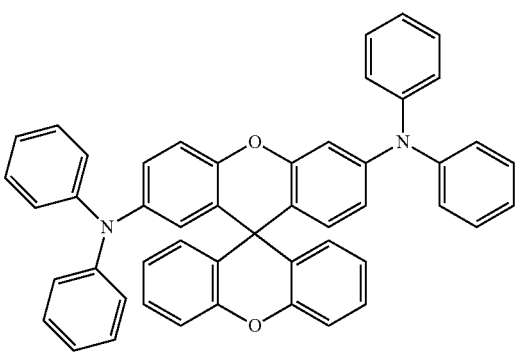
55
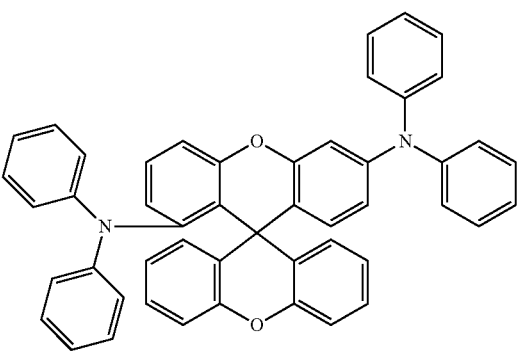
-continued
56
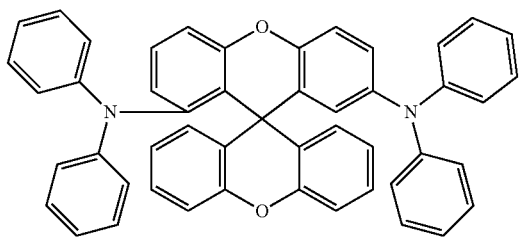
57
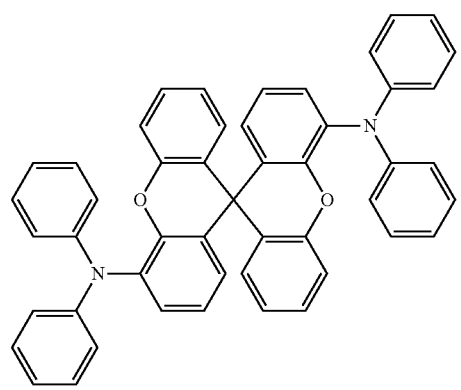
58
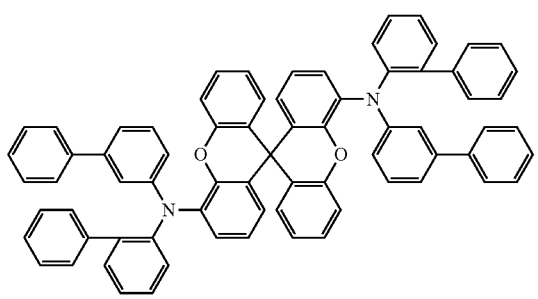
59
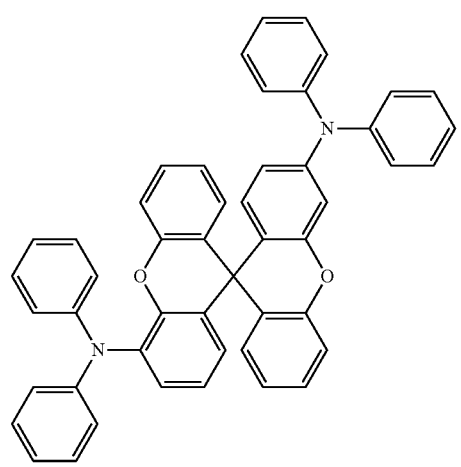

60
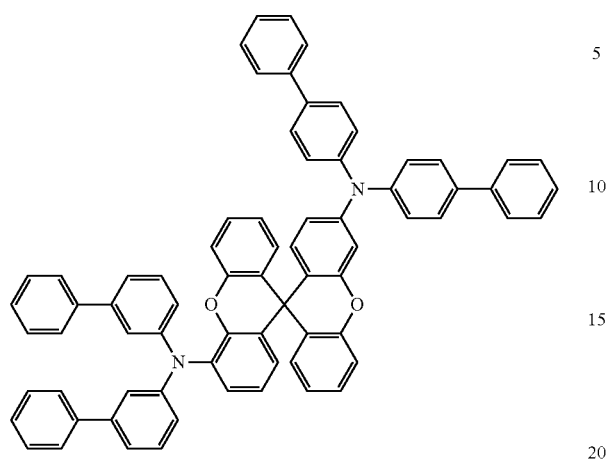
61
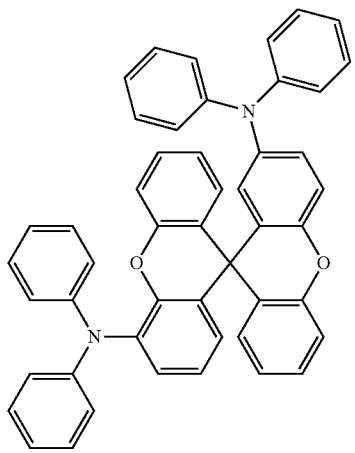
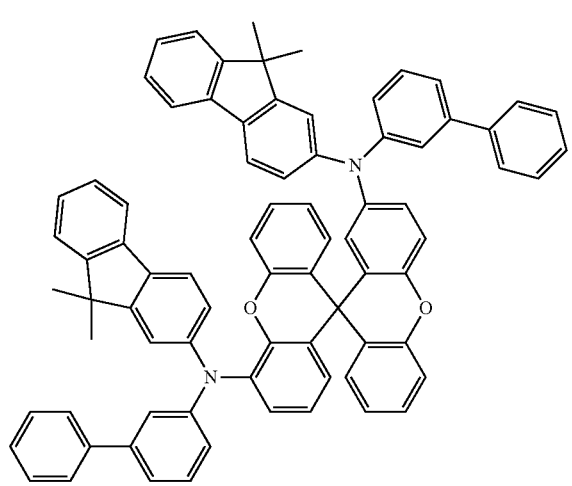
63
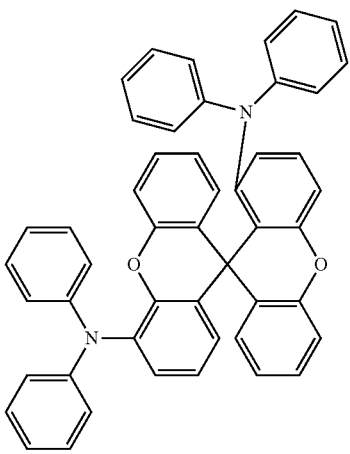
64
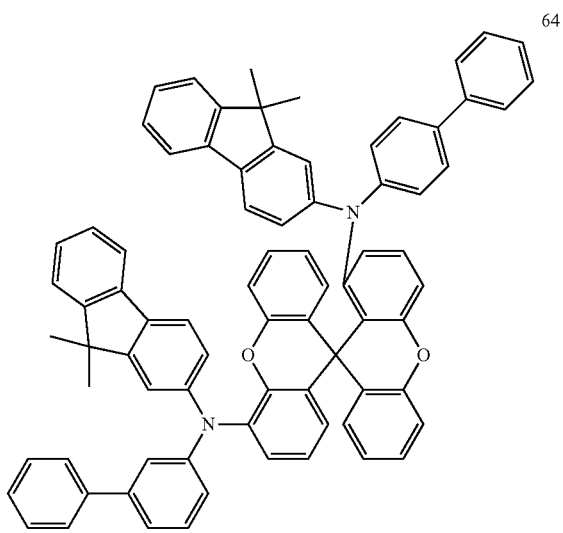
65
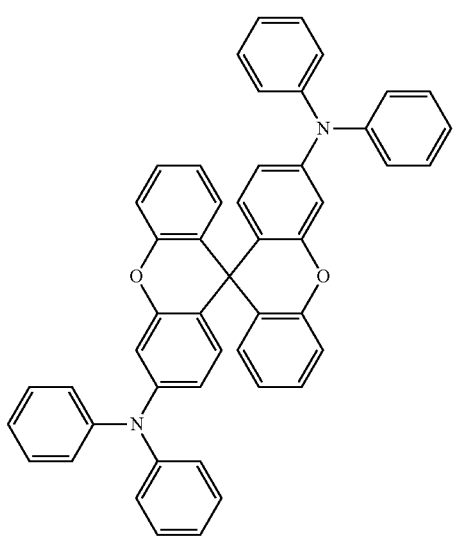

66
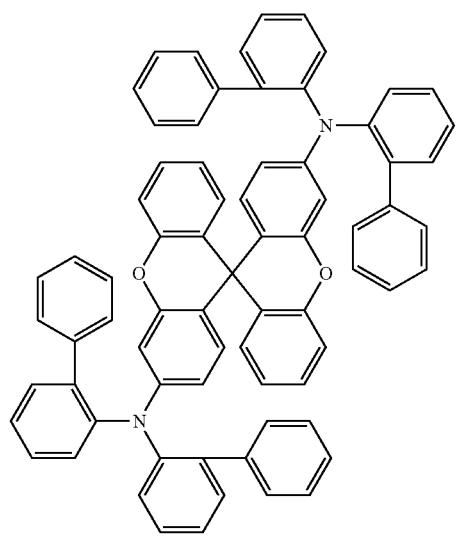
68
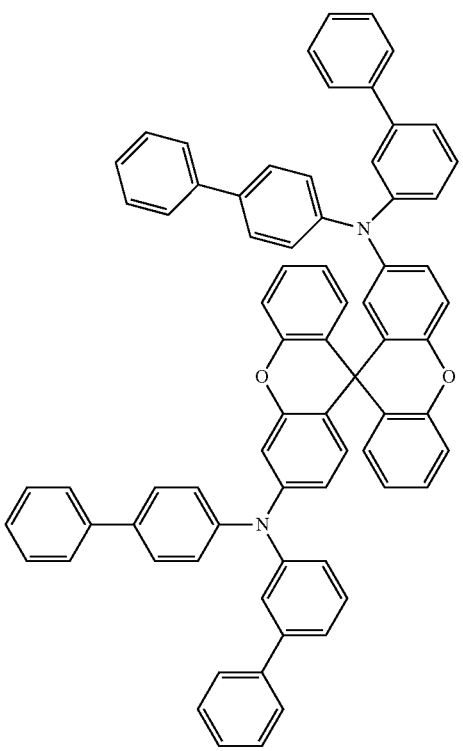
67
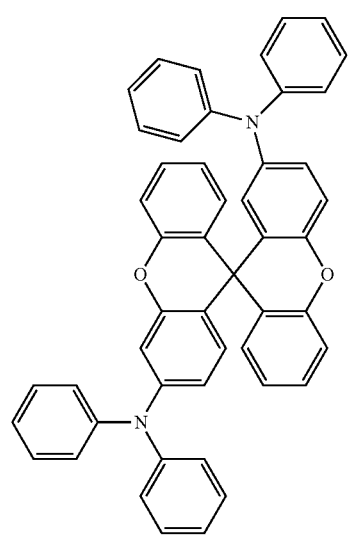
69
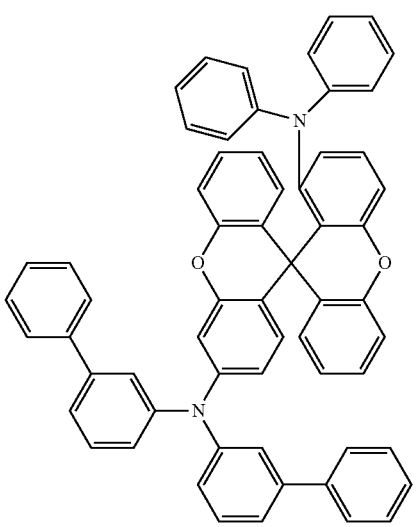

70
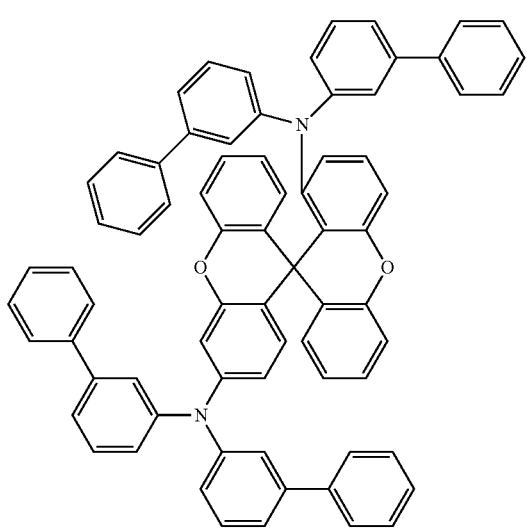
71
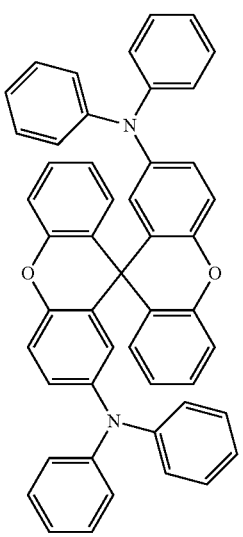
72
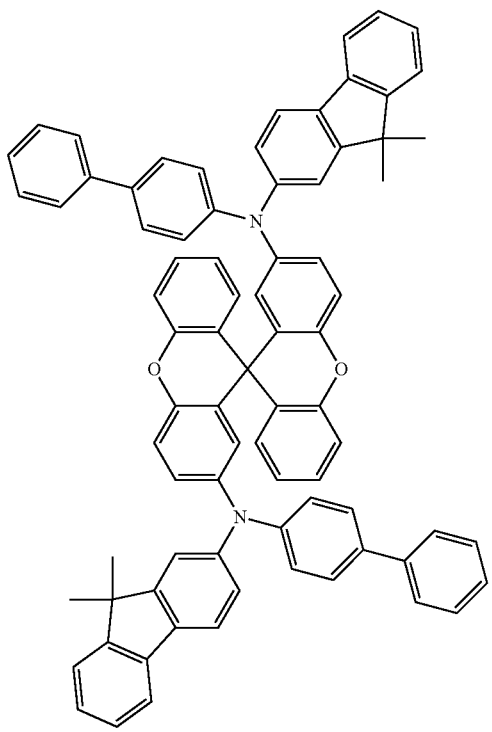
73
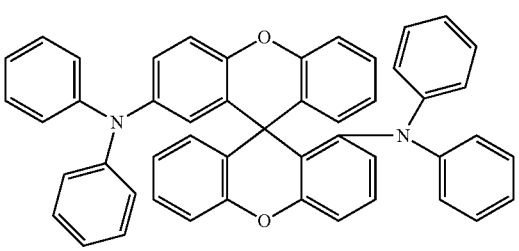
74
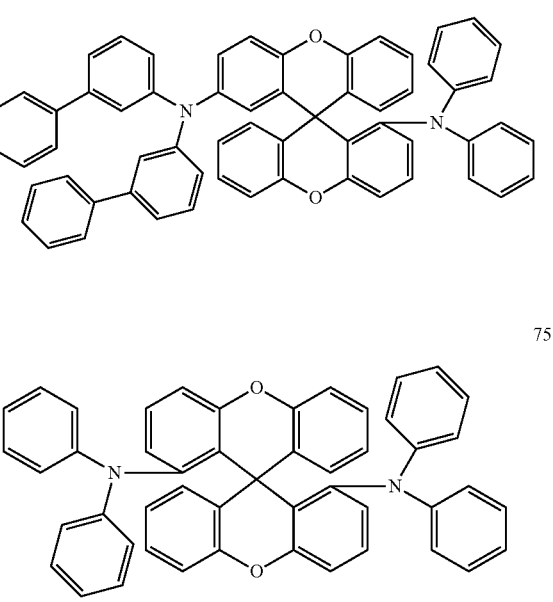
75

76
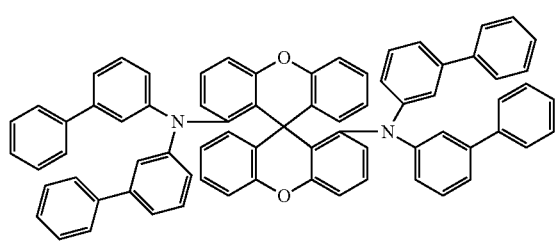
77
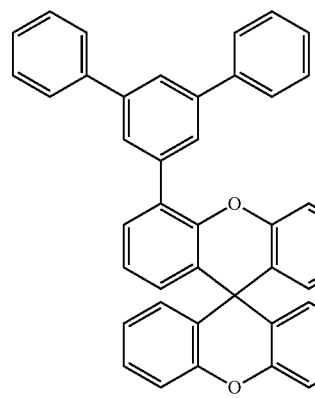
78
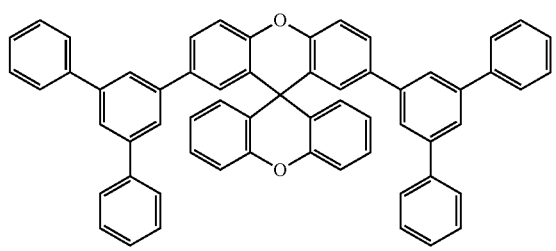
79
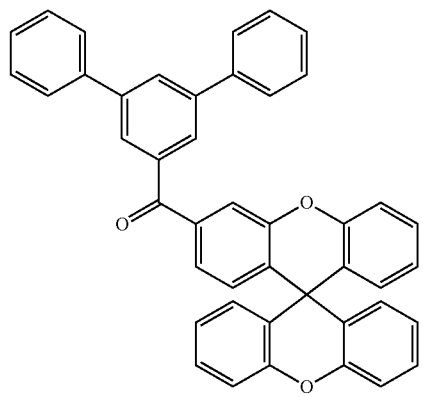
80
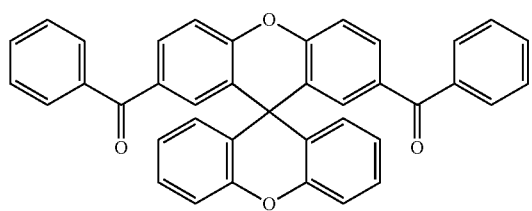
81
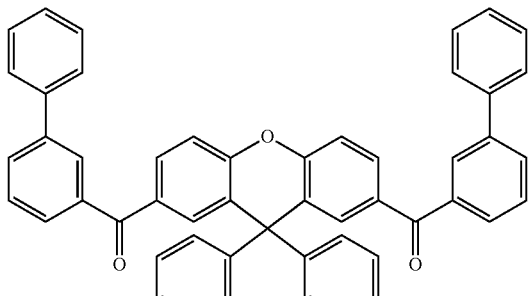
82
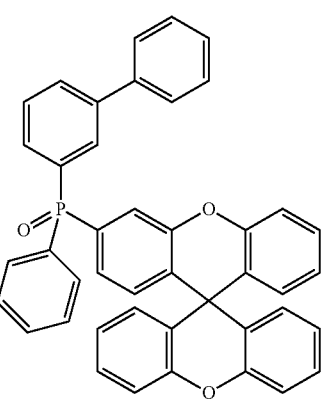
83
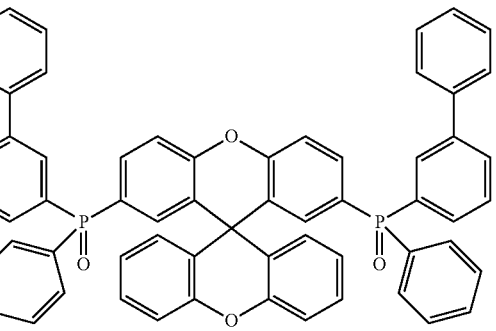
84
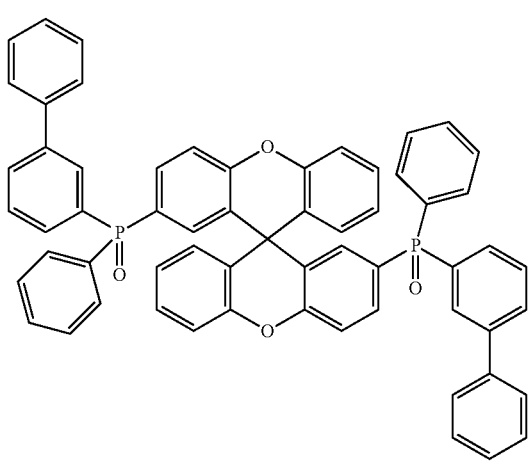

-continued
86
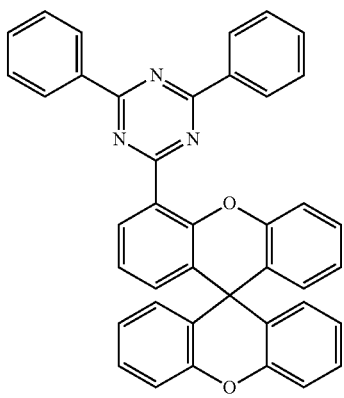
86
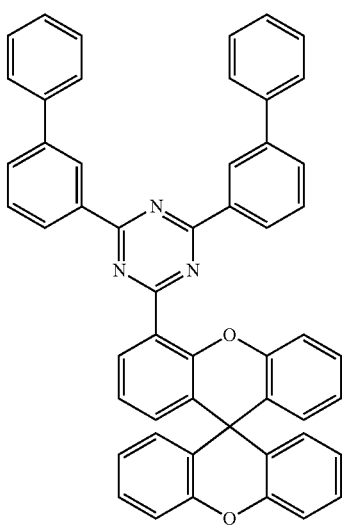
87
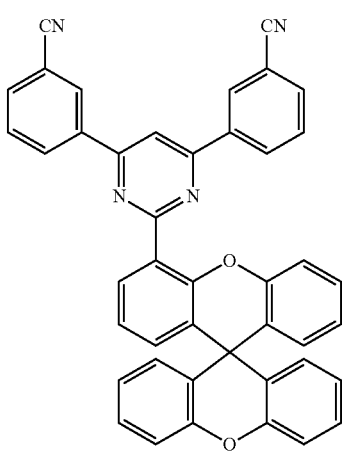
88
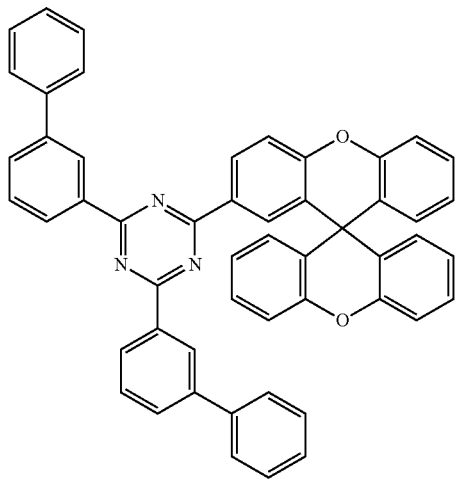
89
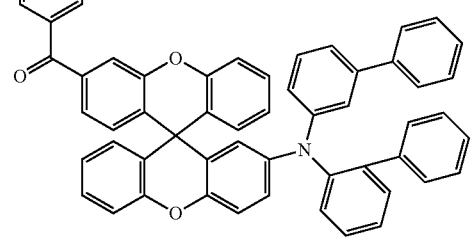
90
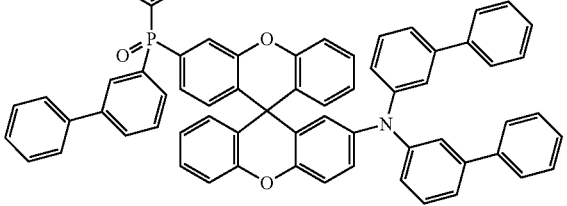
91
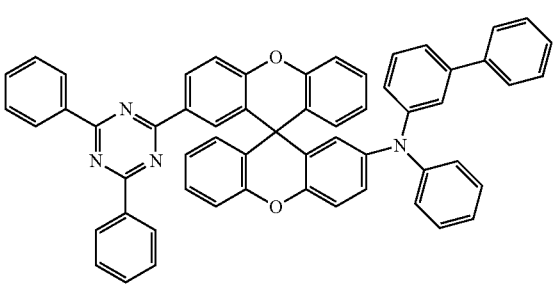

92
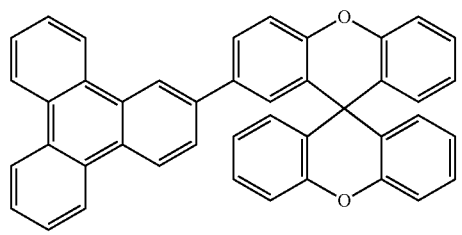
93
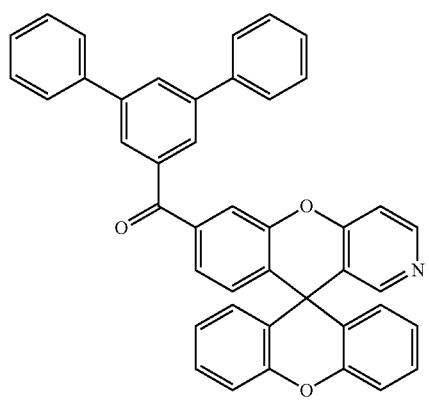
94
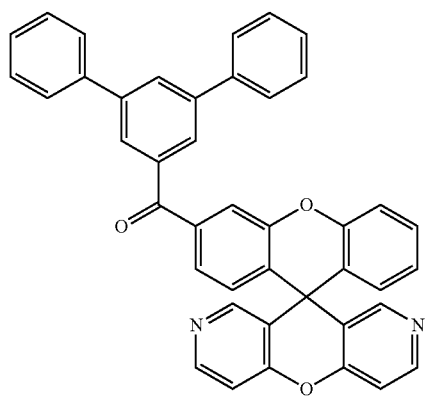
95
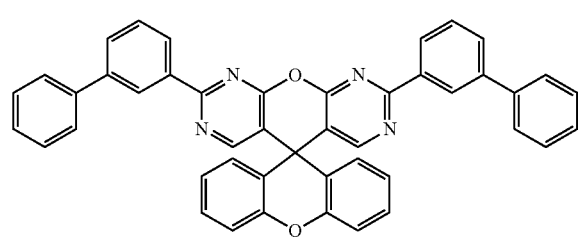
96
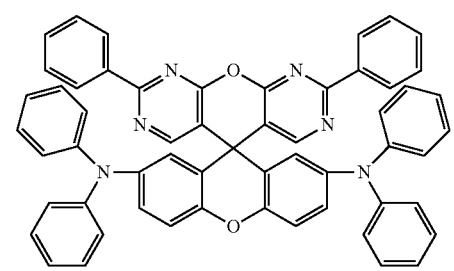
97
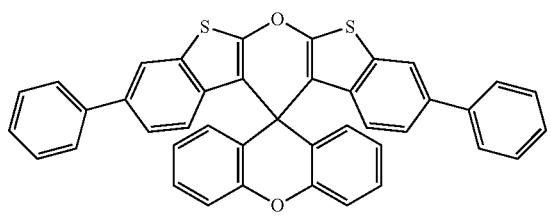
98
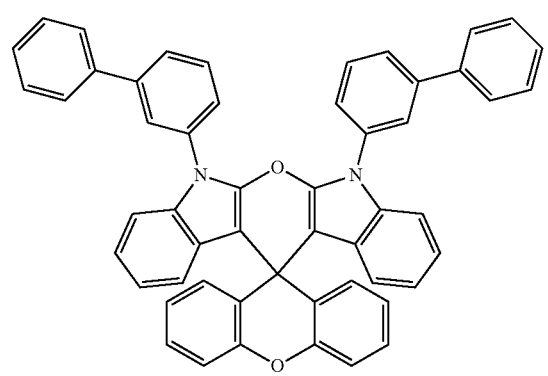
99
100
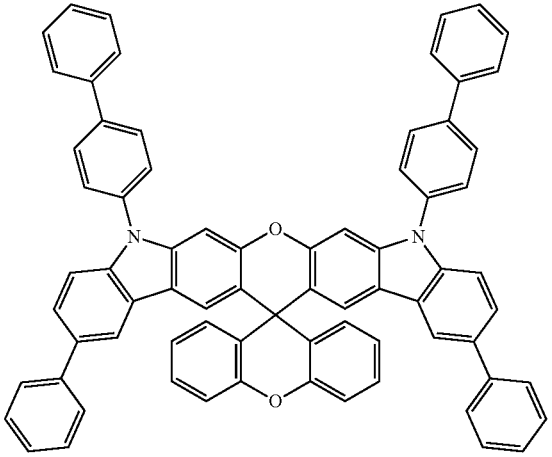

-continued

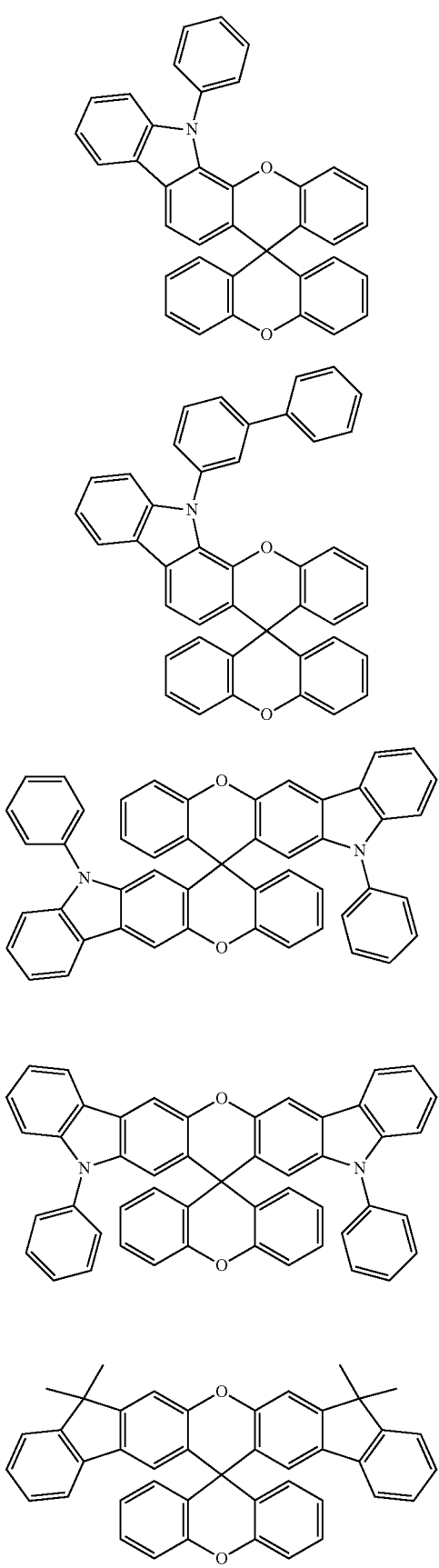

-continued

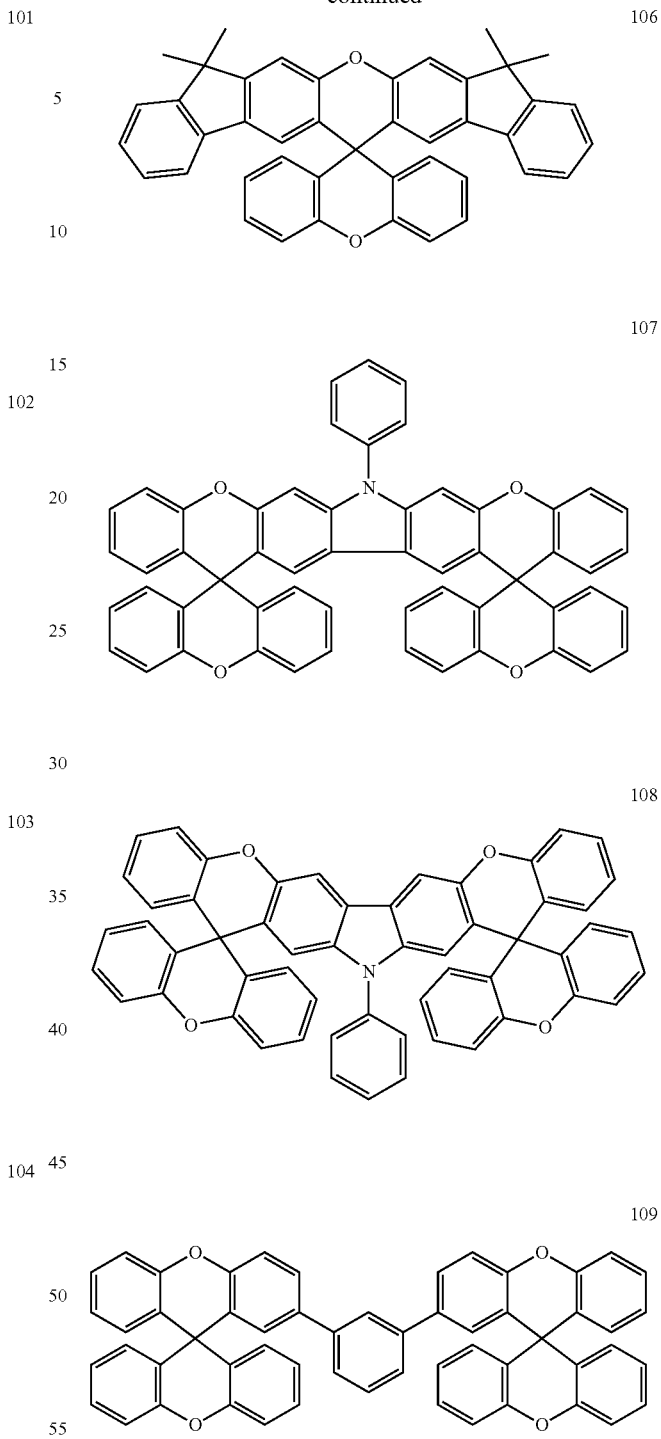

The compounds according to the invention can be prepared by the route outlined in Scheme 1.

The metallation of a 2-halogen-substituted diaryl ether (A), where the halogen is preferably bromine, using reactive metals (for example magnesium by the Grignard method) or using organolithium compounds, followed by addition onto mono-, di or polyhalogenated xanthone (B) and subsequent acid-catalysed cyclisation of the intermediate alcoholate leads to the corresponding halogen-substituted spiro-9,9-bixanthenes (C) (Scheme 1). Hal here stands for a halogen and R for a substituent as defined above for $R^1$.

Scheme 1:

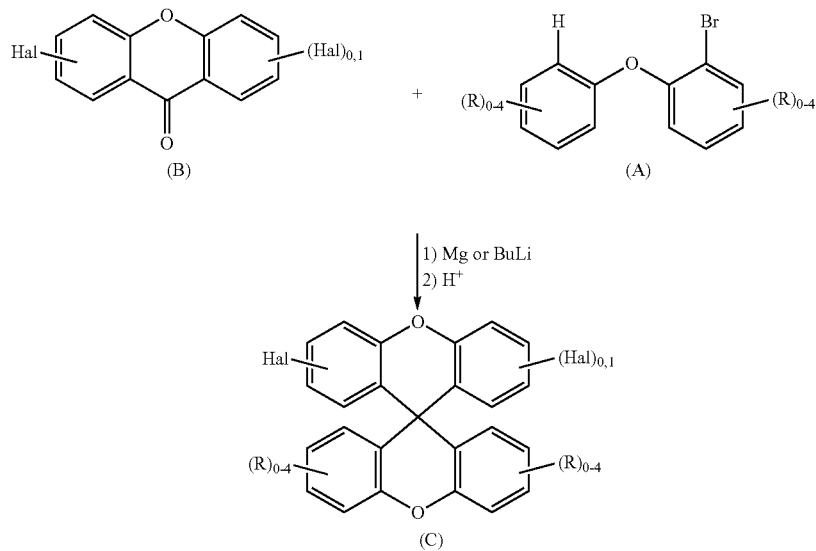

The halides, in particular bromides, (C) formed in this way can subsequently be reacted further by methods familiar to the person skilled in the art, such as, for example, C—C coupling, such as Suzuki, Negishi, Yamamoto, Grignard Cross, Stille, Heck coupling, etc., or C—N coupling, such as Buchwald or Ullmann coupling, sililyation, phosphanylation, boranylation, polycondensation, etc.

The present invention furthermore relates to a process for the preparation of a compound of the formula (1), comprising the reaction steps:
a) synthesis of a halogen-substituted spiro-9,9-bixanthene; and
b) reaction of the halogen-substituted spiro-9,9-bixanthene in a C—C coupling, such as Suzuki, Negishi, Yamamoto, Grignard-Cross, Stille, Heck coupling, etc., or C—N coupling, such as Buchwald or Ullmann coupling, sililyation, phosphanylation, boranylation, polycondensation, etc. . . . .

The compounds according to the invention described above, in particular compounds which are substituted by reactive leaving groups, such as bromine, iodine, chlorine, boronic acid or boronic acid ester, or by reactive, polymerisable groups, such as olefins, styrenes, acrylates or oxetanes, can be used as monomers for the generation of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers containing one or more of the compounds according to the invention indicated above, where one or more bonds from the compound according to the invention to the polymer, oligomer or dendrimer are present at one or more positions instead of substituents. Depending on the linking of the compound according to the invention, this forms a side chain of the oligomer or polymer or is linked in the main chain or forms the core of a dendrimer. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers in which the units of the formula (1) or the preferred embodiments indicated above are present to the extent of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also contain further units, for example hole-transport units, in particular those based on triarylamines, and/or electron-transport units. In addition, the polymers may contain triplet emitters, either copolymerised or mixed in as a blend. In particular, the combination of the oligomers, polymers or dendrimers according to the invention with triplet emitters leads to particularly good results.

The compounds according to the invention are suitable for use in an electronic device, in particular in an organic electroluminescent device.

The present invention therefore furthermore relates to the use of a compound according to the invention in an electronic device, in particular in an organic electroluminescent device.

The present invention still furthermore relates to an electronic device comprising at least one compound according to the invention.

An electronic device in the sense of the present invention is a device which comprises at least one layer which comprises at least one organic compound. The component may also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitised organic solar cells (DSSCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), but preferably organic electroluminescent devices (OLEDs), particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device here may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). The organic electroluminescent device according to the invention may also be a tandem OLED, in particular also for white-emitting OLEDs.

The compound according to the invention in accordance with the embodiments indicated above can be employed in various layers, depending on the precise structure. Preference is given to an organic electroluminescent device comprising a compound of the formula (1) or the preferred embodiments indicated above as matrix material for fluorescent or phosphorescent emitters and/or as fluorescent emitters, in particular for blue-fluorescent emitters, and/or in an electron-blocking or exciton-blocking layer and/or in a hole-transport layer and/or in a hole-blocking layer and/or in an electron-transport layer, depending on the precise substitution.

In a further embodiment of the invention, the organic electroluminescent device comprises the compound according to the invention in an optical coupling-out layer. An optical coupling-out layer here is taken to mean a layer which is not located between the anode and the cathode, but instead is applied to an electrode outside the actual device, for example between an electrode and a substrate, in order to improve the optical coupling-out.

In a preferred embodiment of the invention, the compound according to the invention is employed as matrix material for a fluorescent or phosphorescent compound, in particular for a phosphorescent compound, in an emitting layer. The organic electroluminescent device here may comprise one emitting layer, or it may comprise a plurality of emitting layers, where at least one emitting layer comprises at least one compound according to the invention as matrix material.

If the compound according to the invention is employed as matrix material for an emitting compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state >1, in particular from an excited triplet state. In the sense of this application, all luminescent complexes containing transition metals or lanthanides, in particular all iridium, platinum and copper complexes, are to be regarded as phosphorescent compounds.

The mixture of the compound according to the invention and the emitting compound comprises between 99 and 1% by vol., preferably between 98 and 10% by vol., particularly preferably between 97 and 60% by vol., in particular between 95 and 80% by vol., of the compound according to the invention, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527, WO 2008/086851 or the unpublished application EP 11007693.2, indolocarbazole derivatives, for example in accordance with WO 2007/063754 or WO 2008/056746, indenocarbazole derivatives, for example in accordance with WO 2010/136109 or WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306, WO 2011/057706, WO 2011/060859 or WO 2011/060877, zinc complexes, for example in accordance with EP 652273 or WO 2009/062578, diazasilole or tetraazasilole derivatives, for example in accordance with WO 2010/054729, diaza-phosphole derivatives, for example in accordance with WO 2010/054730, bridged carbazole derivatives, for example in accordance with WO 2011/042107, WO 2011/060867, WO 2011/088877 and the unpublished application EP 11003232.3, or triphenylene derivatives, for example in accordance with the unpublished application DE 102010048608.6. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339 and WO 2012/007086. Also suitable are, for example, the metal complexes disclosed in the unpublished applications EP 11004545.7, EP 11005252.9 and EP 11006562.0. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is the same as or similar to the metal complex in the emitting layer as hole-transport or hole-injection material directly adjacent to the emitting layer, as described, for example, in WO 2009/030981.

In a further embodiment of the invention, the compound according to the invention is employed in a hole-transport layer or in an electron-blocking layer or exciton-blocking layer.

In still a further preferred embodiment of the invention, the compound according to the invention is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, LiQ (lithium hydroxy-quinolinate).

In still a further preferred embodiment of the invention, the compound according to the invention is employed in a hole-blocking layer. A hole-blocking layer is taken to mean a layer which is directly adjacent to an emitting layer on the cathode side.

In the further layers of the organic electroluminescent device according to the invention, all materials can be used as are usually employed in accordance with the prior art. The person skilled in the art will therefore be able to employ all materials which are known for organic electroluminescent devices in combination with the compounds of the formula (1) according to the invention or the preferred embodiments indicated above without inventive step.

Preference is furthermore given to an organic electroluminescent device, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished by one or more of the following surprising advantages over the prior art:

1. The compounds according to the invention or compounds of the formula (1) or the preferred embodiments indicated above, employed as matrix material for fluorescent or phosphorescent emitters, result in high efficiencies and in long lifetimes. This applies, in particular, if the compounds are employed as matrix material for a phosphorescent emitter.
2. The compounds according to the invention or compounds of the formula (1) or the preferred embodiments indicated above are suitable not only as matrix for red-phosphorescent compounds, but also for green- and possibly also for blue-phosphorescent compounds.
3. The compounds according to the invention can be prepared in very high yield and very high purity, which means that complex purification, which is always also associated with losses of material, can be omitted or at least is only necessary to a considerably reduced extent.
4. The compounds according to the invention have high thermal stability, which offers advantages not only in the production of the OLEDs by vacuum evaporation, but also in the purification by sublimation methods.

These above-mentioned advantages are not accompanied by an impairment in the other electronic properties.

The invention is explained in greater detail by the following examples without wishing to restrict it thereby. The person skilled in the art will be able to use the descriptions to carry out the invention throughout the range disclosed and prepare further compounds according to the invention without inventive step and use them in electronic devices or apply the process according to the invention.

EXAMPLES

The following syntheses are carried out, unless indicated otherwise, under a protective-gas atmosphere in dried solvents. The solvents and reagents can be purchased from ALDRICH or ABCR. The numbers indicated in the case of the starting materials which are not commercially available are the corresponding CAS numbers.

Example 1

2,7-Dibromosipro-9,9'-bixanthene, synthone S1

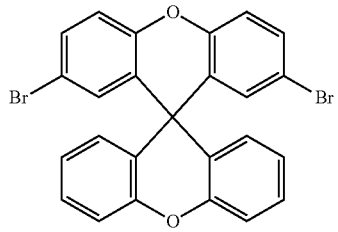

The corresponding Grignard reagent is prepared from 95.6 g (380 mmol) of 2-bromophenyl phenyl ether [7025-06-1] in a mixture of 2.6 ml (34 mmol) of 1,2-dichloroethane and 1000 ml of THF with 10.8 g (410 mmol) of iodine-activated magnesium turnings. When all the magnesium has reacted, 112.0 g (316 mmol) of 2,7-dibromoxanthone[40102-85-0] in solid form are introduced into the solution in portions, and the reaction mixture is stirred under reflux for a further 6 h. 500 ml of THF are distilled off, the suspension is allowed to cool to 30° C. with stirring, 900 ml of glacial acetic acid are rapidly added dropwise (NOTE: exothermic!), a mixture of 100 ml of glacial acetic acid and 30 ml of conc. sulfuric acid is added dropwise to the red solution, the mixture is stirred at 60° C. for a further 6 h, allowed to cool to 30° C., 600 ml of ethanol and then 400 ml of a mixture of ethanol:water (1:1 v:v) are added dropwise, the mixture is stirred for a further 1 h, the colourless solid is filtered off with suction, washed twice with 150 ml of glacial acetic acid each time, twice with 200 ml of a mixture of ethanol:water (1:1 v:v) each time and dried in vacuo. The solid is taken up in 2000 ml of dichloromethane, insoluble components are filtered off with suction via a short Celite bed, the dichloromethane is removed in vacuo, and the product is then recrystallised once from DMF. Yield: 121.6 g (240 mmol), 76%; purity: about 99.5% according to $^1$H-NMR.

The following compounds are obtained analogously:

-continued

| Ex. | Bromo-diaryl ether | Xanthone | Product | Yield |
|---|---|---|---|---|
| 5 | 1246661-43-7 | | S5 | 68% |
| 6 | 27044-93-5 | | S6 | 70% |
| 7 | 556113-49-6 | | S7 | 66% |

Example 8

2,7-Bis(diphenylamino)sipro-9,9'-spirobixanthene

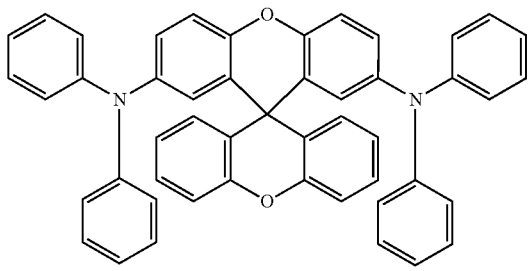 [SMILES: c1ccc(N(c2ccccc2)c2ccc3c(c2)C2(c4ccccc4Oc4ccccc42)c2cc(N(c4ccccc4)c4ccccc4)ccc2O3)cc1]

A mixture of 50.6 g (100 mmol) of 2,7-dibromospiro-9,9'-spirobixanthene S1, 37.2 g (220 mmol) of diphenylamine, 25.0 g (260 mmol) of sodium tert-butoxide, 809 mg (4 mmol) of tri-tert-butylphosphine, 449 mg (2 mmol) of palladium(II) acetate and 1000 ml of toluene is heated under reflux for 16 h. The reaction mixture is allowed to cool to 50° C., 500 ml of water are added, the organic phase is separated off, washed twice with 500 ml of water, dried over magnesium sulfate, filtered through a Celite bed (5 cm) and then evaporated to dryness in vacuo. The crude product is recrystallised twice from DMF and three times from dioxane and finally subjected to fractional sublimation twice (p about $10^{-5}$ mbar, T=330° C.). Yield: 32.9 g (48 mmol) 48%, purity: 99.9% according to HPLC.

The following compounds are obtained analogously, using 200 mmol in the case of monobromides:

| Ex. | Amine | Bromide | Product | Yield |
|---|---|---|---|---|
| 9 | 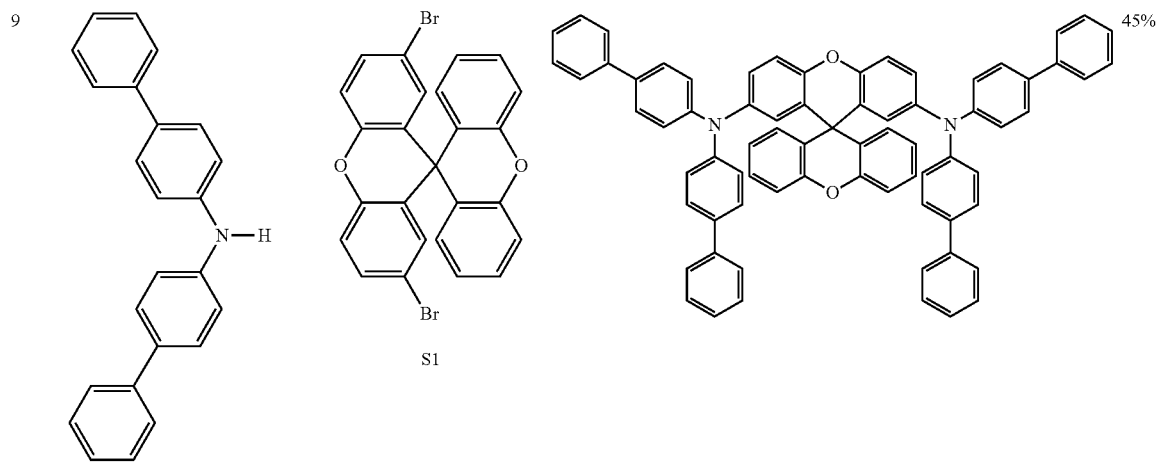 102113-98-4 | | S1 | 45% |
| 10 | 897671-69-1 | | S1 | 51% |
| 11 | 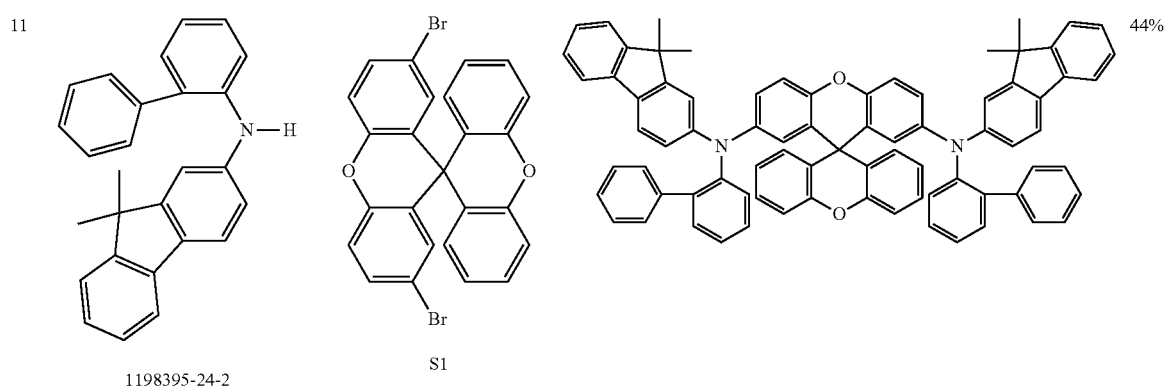 1198395-24-2 | | S1 | 44% |
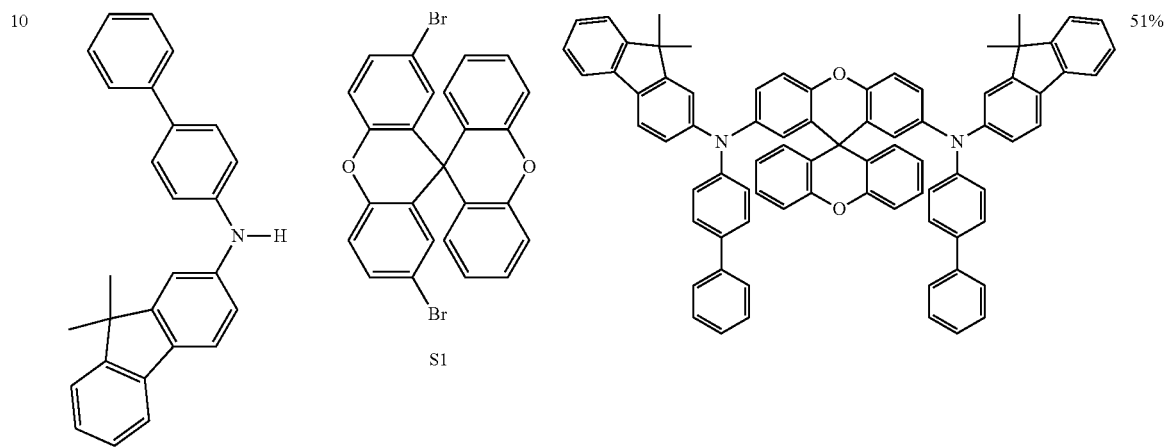

-continued

| Ex. | Amine | Bromide | Product | Yield |
|---|---|---|---|---|
| 12 | 102113-98-4 | S2 | | 50% |
| 13 | 169224-65-1 | S2 | | 46% |
| 14 | | S3 | | 45% |

-continued

| Ex. | Amine | Bromide | Product | Yield |
|---|---|---|---|---|
| 15 | | S3 | | 46% |
| 16 | 1198395-24-2 | S4 | | 41% |
| 17 | 5369-25-5 | S4 | | 49% |
| 18 | 1198395-24-2 | S5 | | 42% |

-continued
| Ex. | Amine | Bromide | Product | Yield |
|---|---|---|---|---|
| 19 | 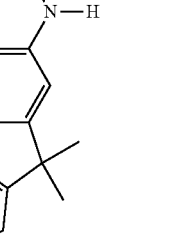 1198395-24-2 | 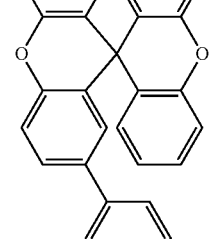 S6 | 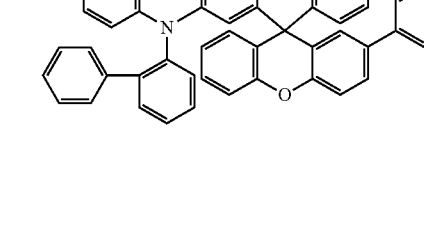 | 46% |
| 20 | 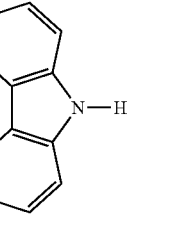 86-74-8 | 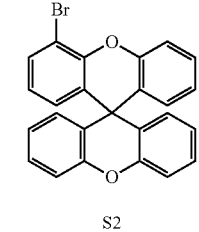 S2 | 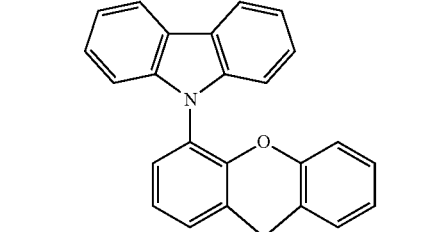 Potassium carbonate is used instead of sodium tert-butoxide, o-xylene is used instead of toluene. | 50% |
| 21 | 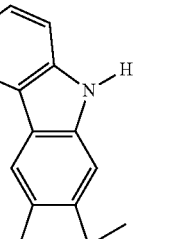 1257220-47-5 | 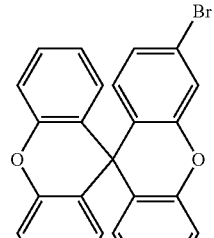 S3 | 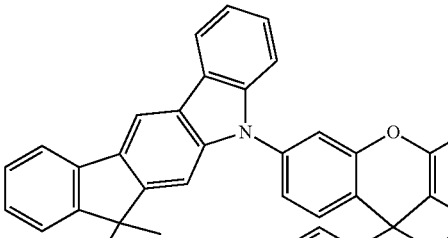 Potassium carbonate is used instead of sodium tert-butoxide, o-xylene is used instead of toluene. | 38% |

Example 22

2,7-Dibromosipro-9,9'-spirobixanthene

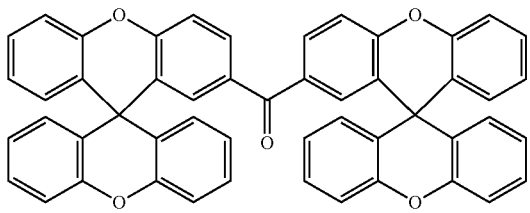 [SMILES: O=C(c1ccc2c(c1)C1(c3ccccc3Oc3ccccc31)c1ccccc1O2)c1ccc2c(c1)C1(c3ccccc3Oc3ccccc31)c1ccccc1O2]

40 ml (100 mmol) of n-butyllithium (2.5M in n-hexane) are added dropwise to a solution, cooled to −78° C., of 42.7 g (100 mmol) of 2-bromospiro-9,9'-spirobixanthene S4 in 1500 ml of THF, and the mixture is stirred for a further 30 min. 4.6 ml (50 mmol) of N,N-dimethylcarbamoyl chloride [79-44-7], diluted with 10 ml of THF, are then added in one portion, the reaction mixture is stirred for a further 30 min., allowed to warm to 0° C., 50 ml of conc. hydrochloric acid are added, and the reaction mixture is heated under reflux for 5 h. After cooling, the THF is removed in vacuo, the residue is taken up in 200 ml of ethanol, rendered weakly alkaline using 10% ammonia solution, the solid which has precipitated out is filtered off with suction, washed three times with 100 ml of an ethanol/water mixture (1:1 vv) each time and finally washed once with 50 ml of ethanol. The crude product is recrystallised five times from DMF and finally subjected to fractional sublimation twice (p about $10^{-5}$ mbar, T=340° C.). Yield: 19.5 g (27 mmol) 54%, purity: 999% according to HPLC.

The following compounds are obtained analogously:

| Ex. | Electrophile | Bromide | Product | Yield |
|---|---|---|---|---|
| 23 | | S3 | | 57% |
| 24 | 1351669-38-9<br>100 mmol of electrophile | S2 | The hydrolysis step with conc. HCl is omitted. | 42% |
| 25 | 1499-21-4 | S3 | The hydrolysis step with conc. HCl is omitted. | 58% |

-continued

| Ex. | Electrophile | Bromide | Product | Yield |
|---|---|---|---|---|
| 26 | 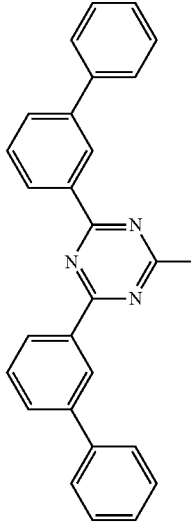<br>1205748-61-3<br>100 mmol of electrophile | 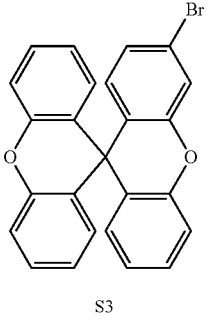<br>S3 | 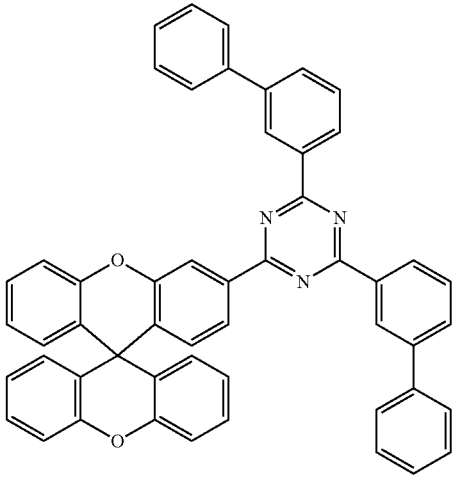 [SMILES: c1ccc(-c2cccc(-c3nc(-c4cccc(-c5ccccc5)c4)nc(-c4ccc5c(c4)Oc4ccccc4C54c5ccccc5Oc5ccccc54)n3)c2)cc1]<br>The hydrolysis step with conc. HCl is omitted. | 53% |

Production of the OLEDs

OLEDs according to the invention and OLEDs in accordance with the prior art are produced by a general process in accordance with WO 2004/058911, which is adapted to the circumstances described here (layer-thickness variation, materials).

The structure and data of various OLEDs are presented in the following Examples O1 to O22 (see Tables 1 to 5). Glass plates coated with structured ITO (indium tin oxide) in a thickness of 150 nm are coated with 20 nm of PEDOT (poly (3,4-ethylenedioxy-2,5-thiophene), applied by spin coating from water; purchased from H. C. Starck, Goslar, Germany) for improved processing. These coated glass plates form the substrates to which the OLEDs are applied. The OLEDs have in principle the following layer structure: substrate/optional hole-injection layer (HIL)/hole-transport layers (HTL)/interlayer (IL)/electron-blocking layer (EBL)/emission layer (EML)/electron-transport layer (ETL)/optional electron-injection layer (EIL) and finally a cathode. The cathode is formed by an aluminium layer with a thickness of 100 nm. The precise structure of the OLEDs is shown in Tables 1 and 3. The materials required for the production of the OLEDs are shown in Table 5.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as H1:SEB1 (95%:5%) here means that material H1 is present in the layer in a proportion by volume of 95% and SEB1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term U @ 1000 cd/m$^2$ in Table 2 and 4 denotes the voltage required for a luminous density of 1000 cd/m$^2$. Finally, EQE @ 1000 cd/m$^2$ denotes the external quantum efficiency at an operating luminous density of 1000 cd/m$^2$. LT80 @ 6000 cd/m2 is the lifetime until the OLED at a luminosity of 6000 cd/m$^2$ has dropped to 80% of the initial intensity, i.e. to 4800 cd/m$^2$.

The data measured for the various OLEDs are summarised in Tables 2 and 4.

Use of the Compounds According to the Invention in Fluorescent and Phosphorescent OLEDs The compounds according to the invention are suitable, in particular, as HTM (hole-transport material) or EBM (electron-blocking material) in OLEDs. They are suitable for use in a single layer, but also as component of a mixture as HTM, EBM or as constituent of the emitting layer. Compared with comparative devices in accordance with the prior art (V1 and V2), all samples comprising the compounds according to the invention exhibit higher efficiencies and/or improved lifetimes. Compared with reference material NPB, the compounds according to the invention exhibit better efficiencies and better lifetimes.

TABLE 1

Structure of the OLEDs

| Ex. | IL Thickness/nm | HTL Thickness/nm | IL Thickness/nm | HTL2 Thickness/nm | EBL Thickness/nm | EML Thickness/nm | ETL Thickness/nm |
|---|---|---|---|---|---|---|---|
| V1 | HIL1 5 nm | HIL2 130 nm | HIL1 5 nm | NPB 10 nm | NPB 20 nm | H1(95%):SEB1(5%) 20 nm | ETM1(50%):LiQ(50%) 30 nm |
| O1 | HIL1 5 nm | HIL2 130 nm | HIL1 5 nm | NPB 10 nm | Ex. 8 20 nm | H1(95%):SEB1(5%) 20 nm | ETM1(50%):LiQ(50%) 30 nm |
| O2 | HIL1 5 nm | HIL2 130 nm | HIL1 5 nm | — | Ex. 9 30 nm | H1(95%):SEB1(5%) 20 nm | ETM1(50%):LiQ(50%) 30 nm |
| O3 | HIL1 5 nm | HIL2 130 nm | HIL1 5 nm | — | Ex. 10 20 nm | H1(95%):SEB1(5%) 20 nm | ETM1(50%):LiQ(50%) 30 nm |
| O4 | HIL1 5 nm | HIL2 130 nm | HIL1 5 nm | — | Ex. 11 30 nm | H1(95%):SEB1(5%) 20 nm | ETM1(50%):LiQ(50%) 30 nm |
| O5 | HIL1 5 nm | HIL2 130 nm | HIL1 5 nm | — | Ex. 12 30 nm | H1(95%):SEB1(5%) 20 nm | ETM1(50%):LiQ(50%) 30 nm |
| O6 | HIL1 5 nm | HIL2 130 nm | HIL1 5 nm | — | Ex. 13 30 nm | H1(95%):SEB1(5%) 20 nm | ETM1(50%):LiQ(50%) 30 nm |
| O7 | HIL1 5 nm | HIL2 130 nm | HIL1 5 nm | — | Ex. 14 30 nm | H1(95%):SEB1(5%) 20 nm | ETM1(50%):LiQ(50%) 30 nm |
| O8 | HIL1 5 nm | HIL2 130 nm | HIL1 5 nm | — | Ex. 15 30 nm | H1(95%):SEB1(5%) 20 nm | ETM1(50%):LiQ(50%) 30 nm |
| O9 | HIL1 5 nm | HIL2 130 nm | HIL1 5 nm | — | Ex. 16 30 nm | H1(95%):SEB1(5%) 20 nm | ETM1(50%):LiQ(50%) 30 nm |
| O10 | HIL1 5 nm | HIL2 130 nm | HIL1 5 nm | — | Ex. 17 30 nm | H1(95%):SEB1(5%) 20 nm | ETM1(50%):LiQ(50%) 30 nm |
| O11 | HIL1 5 nm | HIL2 130 nm | HIL1 5 nm | — | Ex. 18 30 nm | H1(95%):SEB1(5%) 20 nm | ETM1(50%):LiQ(50%) 30 nm |
| O12 | HIL1 5 nm | HIL2 130 nm | HIL1 5 nm | — | Ex. 19 30 nm | H1(95%):SEB1(5%) 20 nm | ETM1(50%):LiQ(50%) 30 nm |

TABLE 2

Data of the OLEDs

| Ex. | U @ 1000 cd/m2 V | EQE @ 1000 cd/m2 % | LT80 @ 6000 cd/m² [h] | CIE x | CIE y |
|---|---|---|---|---|---|
| V1 | 4.7 | 4.8 | 70 | 0.14 | 0.17 |
| O1 | 4.3 | 6.7 | 80 | 0.14 | 0.16 |
| O2 | 4.3 | 6.6 | 100 | 0.14 | 0.16 |
| O3 | 4.4 | 6.4 | 95 | 0.14 | 0.16 |
| O4 | 4.4 | 7.2 | 105 | 0.14 | 0.16 |
| O5 | 4.4 | 6.9 | 120 | 0.14 | 0.16 |
| O6 | 4.4 | 7.0 | 110 | 0.14 | 0.16 |
| O7 | 4.5 | 7.0 | 120 | 0.14 | 0.16 |
| O8 | 4.4 | 7.1 | 125 | 0.14 | 0.16 |
| O9 | 4.6 | 7.3 | 130 | 0.14 | 0.16 |
| O10 | 4.6 | 6.7 | 85 | 0.14 | 0.16 |
| O11 | 4.3 | 7.1 | 115 | 0.14 | 0.16 |
| O12 | 4.5 | 7.0 | 120 | 0.14 | 0.16 |

TABLE 3

Structure of the OLEDs

| Ex. | HTL Thickness/nm | IL Thickness/nm | HTL2 Thickness/nm | EBL Thickness/nm | EML Thickness/nm | ETL Thickness/nm |
|---|---|---|---|---|---|---|
| V2 | HIL2 70 nm | HIL1 5 nm | — | NPB 90 nm | H2(88%):Irpy(12%) 30 nm | ETM1(50%):LiQ(50%) 40 nm |
| O13 | HIL2 70 nm | HIL1 5 nm | — | Ex. 14 80 nm | H2(88%):Irpy(12%) 30 nm | ETM1(50%):LiQ(50%) 40 nm |
| O14 | HIL2 70 nm | HIL1 5 nm | — | Ex. 15 80 nm | H2(88%):Irpy(12%) 30 nm | ETM1(50%):LiQ(50%) 40 nm |
| O15 | HIL2 70 nm | HIL1 5 nm | — | Ex. 15 90 nm | H3(30%):Ex. 22(65%):Irpy(5%) 30 nm | ETM1(50%):LiQ(50%) 40 nm |
| O16 | HIL2 70 nm | HIL1 5 nm | — | Ex. 15 90 nm | H3(20%):Ex. 23(75%):Irpy(5%) 30 nm | ETM1(50%):LiQ(50%) 40 nm |
| O17 | HIL2 70 nm | HIL1 5 nm | — | Ex. 15 90 nm | H3(30%):Ex. 24(65%):Irpy(5%) 30 nm | ETM1(50%):LiQ(50%) 40 nm |

TABLE 3-continued

Structure of the OLEDs

| Ex. | HTL Thickness/nm | IL Thickness/nm | HTL2 Thickness/nm | EBL Thickness/nm | EML Thickness/nm | ETL Thickness/nm |
|---|---|---|---|---|---|---|
| O18 | HIL2 70 nm | HIL1 5 nm | — | Ex. 15 90 nm | H3(30%):Ex. 25(65%):Irpy(5%) 30 nm | ETM1(50%):LiQ(50%) 40 nm |
| O19 | HIL2 70 nm | HIL1 5 nm | — | Ex. 15 90 nm | H3(25%):Ex. 26(70%):Irpy(5%) 30 nm | ETM1(50%):LiQ(50%) 40 nm |
| O20 | HIL2 70 nm | HIL1 5 nm | — | Ex. 15 90 nm | Ex. 15(30%):Ex. 26(65%):Irpy(5%) 30 nm | ETM1(50%):LiQ(50%) 40 nm |
| O21 | HIL2 70 nm | HIL1 5 nm | — | Ex. 14 80 nm | Ex. 20(88%):Irpy(12%) 30 nm | ETM1(50%):LiQ(50%) 40 nm |
| O22 | HIL2 70 nm | HIL1 5 nm | — | Ex. 14 80 nm | Ex. 21(88%):Irpy(12%) 30 nm | ETM1(50%):LiQ(50%) 40 nm |

TABLE 4

Data of the OLEDs

| Ex. | U @ 1000 cd/m2 V | EQE @ 1000 cd/m2 % | LT80 @ 8000 cd/m$^2$ [h] | CIE x | CIE y |
|---|---|---|---|---|---|
| V2 | 3.5 | 14.4 | 90 | 0.32 | 0.63 |
| O13 | 3.3 | 18.5 | 120 | 0.33 | 0.63 |
| O14 | 3.3 | 18.7 | 130 | 0.33 | 0.63 |
| O15 | 3.2 | 18.9 | 140 | 0.33 | 0.64 |
| O16 | 3.3 | 19.0 | 150 | 0.33 | 0.63 |
| O17 | 3.3 | 18.4 | 110 | 0.33 | 0.64 |
| O18 | 3.6 | 18.7 | 105 | 0.33 | 0.63 |
| O19 | 3.4 | 18.7 | 140 | 0.33 | 0.63 |
| O20 | 3.2 | 18.8 | 135 | 0.33 | 0.64 |
| O21 | 3.4 | 18.0 | 90 | 0.33 | 0.64 |
| O22 | 3.4 | 18.3 | 125 | 0.33 | 0.64 |

TABLE 5

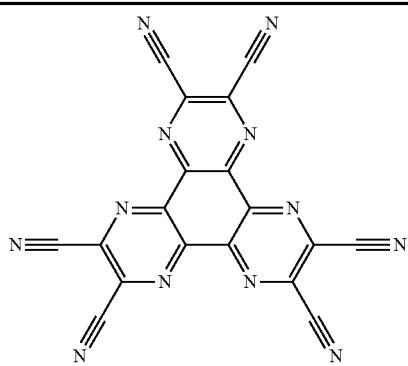

HIL1

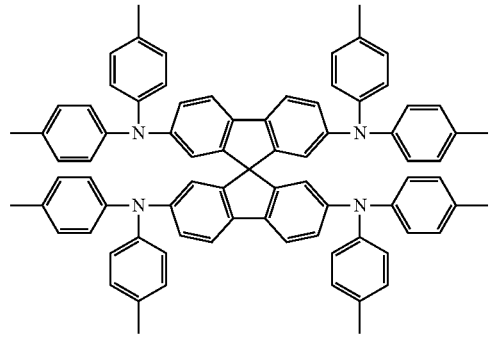

HIL2

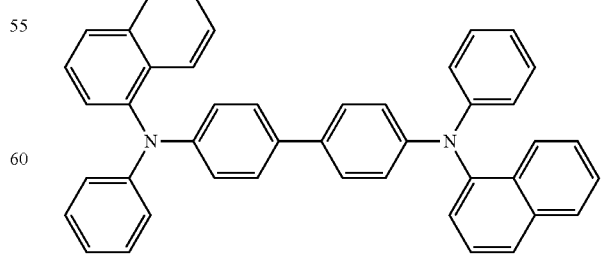

NPB

TABLE 5-continued
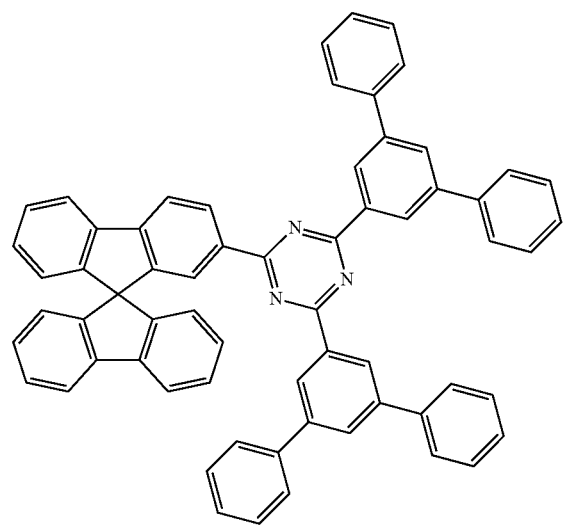 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM1
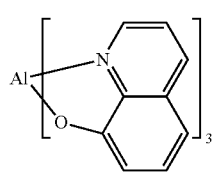
Alq3
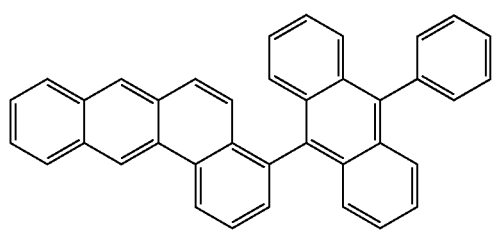 [SMILES: c1ccc(-c2c3ccccc3c(-c3cccc4c3ccc3cc5ccccc5cc34)c3ccccc23)cc1]
H1
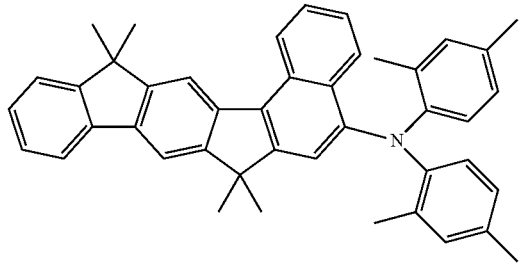 [SMILES: Cc1ccc(N(c2ccc(C)cc2C)c2cc3c(c4ccccc24)-c2cc4c(cc2C3(C)C)-c2ccccc2C4(C)C)c(C)c1]
SEB1
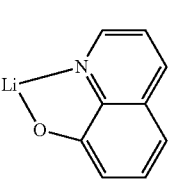
LiQ
TABLE 5-continued
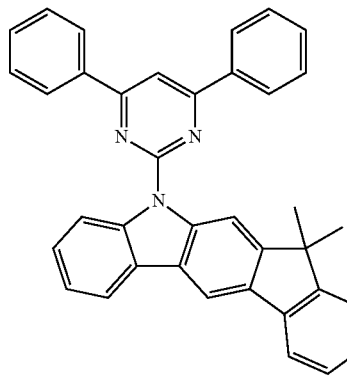
H2
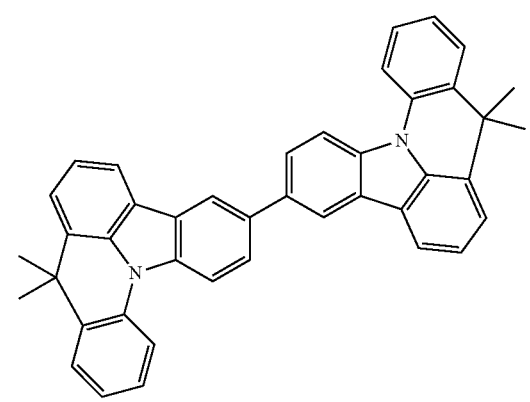
H3
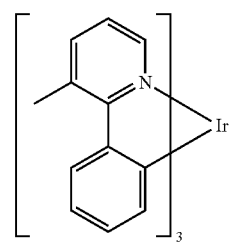
Irpy
The invention claimed is:
1. A compound of the formula (1),
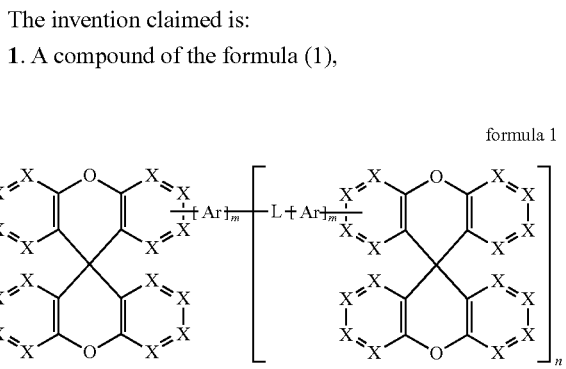
formula 1
where the following applies to the symbols and indices used:

X is on each occurrence, identically or differently, CR¹ or N; where a maximum of one group X per ring stands for N; or two adjacent X stand for a group of the following formula (3),

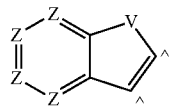

formula (3)

where ^ indicates the corresponding adjacent groups X in the formula (1);

X here stands for C if a group Ar or L is bonded to this group X;

V is on each occurrence, identically or differently, C(R¹)₂, or NR¹;

Z is on each occurrence, identically or differently, CR¹;

Ar is on each occurrence, identically or differently, an aromatic or heteroaromatic ring system having 5 to 40 aromatic ring atoms, which can be substituted by one or more radicals R²; the group Ar and the adjacent group X, which in this case stands for C, can also be bridged to one another here by a single bond or a divalent group selected from C(R²)₂, NR², O or S;

L is on each occurrence, identically or differently, a single bond or a divalent group;

R¹ and R² is selected on each occurrence, identically or differently, from the group consisting of H, D, F, Cl, Br, I, CN, NO₂, N(Ar¹)₂, N(R³)₂, C(=O)Ar¹, C(=O)R³, P(=O)(Ar¹)₂, B(Ar¹)₂, Si(Ar¹)₃, Si(R³)₃, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which can be substituted by one or more radicals R³, where one or more non-adjacent CH₂ groups can be replaced by R³C=CR³, C≡C, Si(R³)₂, C=O, C=S, C=NR³, P(=O)(R³), SO, SO₂, NR³, O, S or CONR³ and where one or more H atoms can be replaced by D, F, Cl, Br, I, CN or NO₂, an aromatic or heteroaromatic ring system having 5 to 60 aromatic ring atoms, which can in each case be substituted by one or more radicals R³, an aryloxy or heteroaryloxy group having 5 to 60 aromatic ring atoms, which can be substituted by one or more radicals R³, where two or more adjacent substituents R¹ or R² can optionally form a monocyclic or polycyclic, aliphatic, aromatic or heteroaromatic ring system, which can be substituted by one or more radicals R³;

wherein if R¹ or R² stand for an aromatic or heteroaromatic ring system, this is selected, identically or differently on each occurrence, from benzene, ortho-, meta- or para-biphenyl, ortho-, meta-, para- or branched terphenyl, ortho-, meta- para- or branched quaterphenyl, 1 or 2-naphthyl, pyrrole, furan, thiophene, indole, benzofuran, benzothiophene, carbazole, dibenzofuran, dibenzothiophene, pyridine, pyrimidine, pyrazine, pyridazine, triazine, anthracene, phenanthrene, pyrene, benzanthracene or combinations of two or three of these groups, each of which can be substituted by one or more radicals R³, Ar¹ is on each occurrence, identically or differently, an aromatic or heteroaromatic ring system having 5-30 aromatic ring atoms, which can be substituted by one or more non-aromatic radicals R³; two radicals Ar¹ here which are bonded to the same N atom or P atom can also be bridged to one another by a single bond or a bridge selected from N(R³), C(R³)₂, O or S;

R³ is selected on each occurrence, identically or differently, from the group consisting of H, D, F, Cl, Br, I, CN, NO₂, N(R⁴)₂, C(=O)R⁴, P(=O)(R⁴)₂, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which can be substituted by one or more radicals R⁴, where one or more non-adjacent CH₂ groups can be replaced by R⁴C=CR⁴, C≡C, Si(R⁴)₂, C=O, C=S, C=NR⁴, P(=O)(R⁴), SO, SO₂, NR⁴, O, S or CONR⁴ and where one or more H atoms can be replaced by D, F, Cl, Br, I, CN or NO₂, an aromatic or heteroaromatic ring system having 5 to 60 aromatic ring atoms, which can in each case be substituted by one or more radicals R⁴, an aryloxy or heteroaryloxy group having 5 to 60 aromatic ring atoms, which can be substituted by one or more radicals R⁴, or a combination of these systems, where two or more adjacent substituents R³ can optionally form a monocyclic or polycyclic, aliphatic ring system, which can be substituted by one or more radicals R⁴;

R⁴ is selected on each occurrence, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms can be replaced by D, F, Cl, Br, I or CN, where two or more adjacent substituents R⁴ can form a mono- or polycyclic, aliphatic ring system with one another;

m is on each occurrence, identically or differently, 0 or 1;

n is 0, 1, 2, 3, 4 or 5;

with the proviso that for n=0, at least one substituent R¹ is present which is selected from the group consisting of CN, N(Ar¹)₂, C(=O)Ar¹, P(=O)(Ar¹)₂, B(Ar¹)₂, Si(Ar¹)₃, Si(R³)₃ or an aromatic or heteroaromatic ring system having 5 to 60 aromatic ring atoms, which can in each case be substituted by one or more radicals R³;

compounds of the formula (1) in which n=0 and four substituents R¹ stand, identically or differently, for an optionally substituted carbazole or diphenylamine, which is in each case bonded to the skeleton via the nitrogen atom, are excluded.

2. The compound according to claim 1, wherein the compound is selected from the compounds of the formula (1a), (1b), (1c) or (1d),

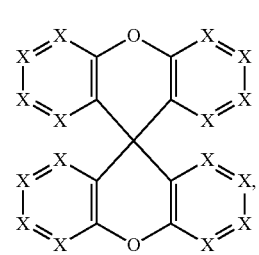

formula (1a)

-continued
formula (1b)
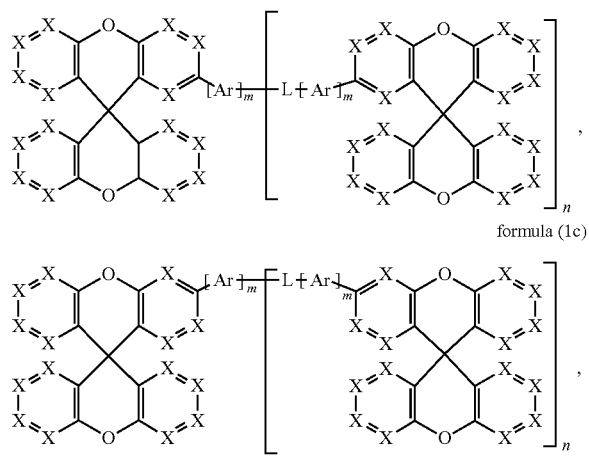
formula (1c)
formula (1d)
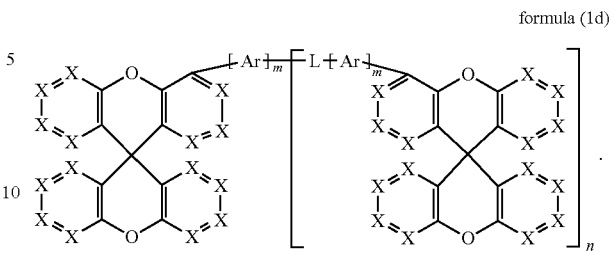
3. The compound according to claim 1, wherein the compound is of one of the formulae (5) to (8),
formula (5)
formula (6)
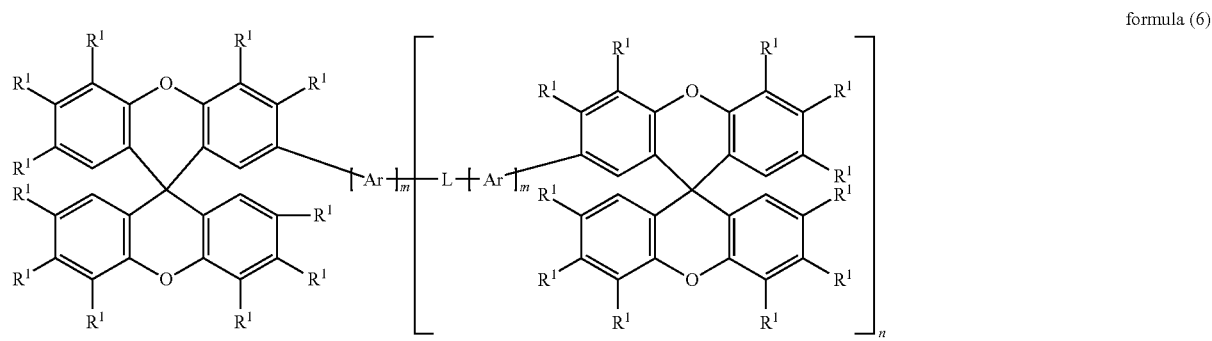
formula (7)
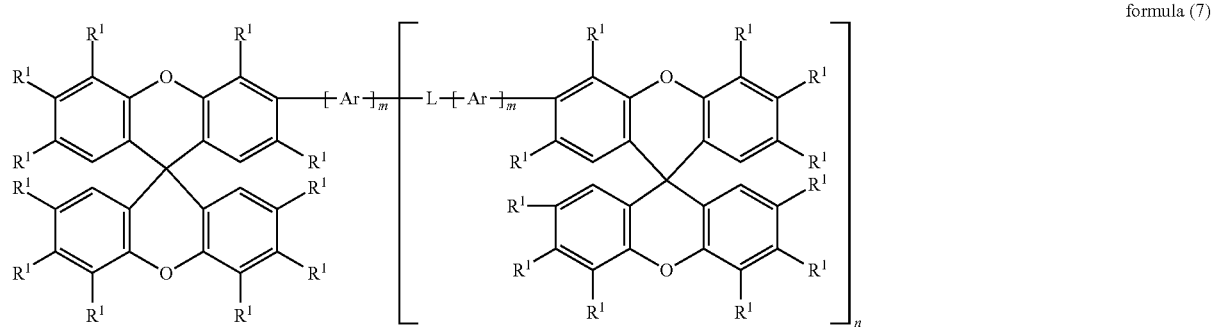

formula (8)
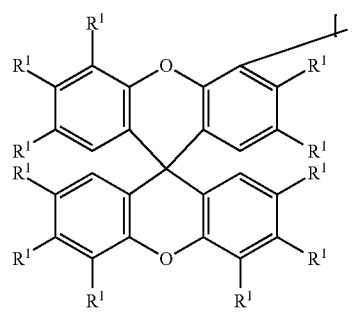 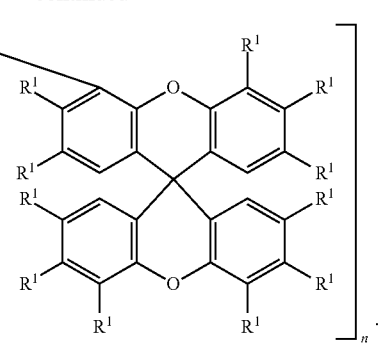
4. A compound selected from the compounds of the formulae (5a) to (5u),
formula (5a)
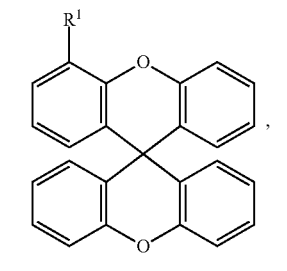
formula (5b)
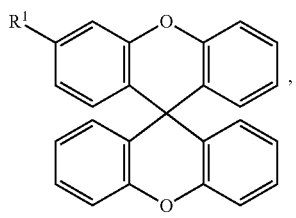
formula (5c)
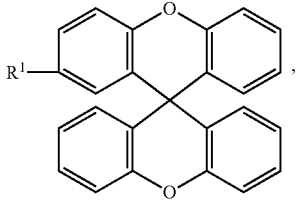
formula (5d)
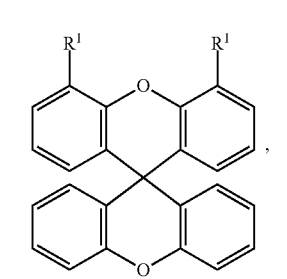
formula (5e)
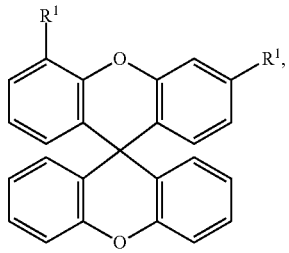
formula (5f)
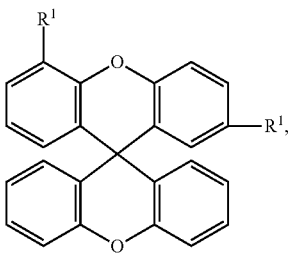
formula (5g)
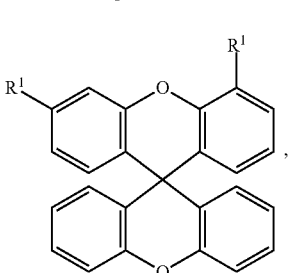
formula (5h)
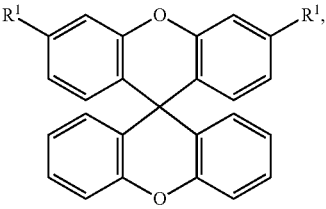
formula (5i)
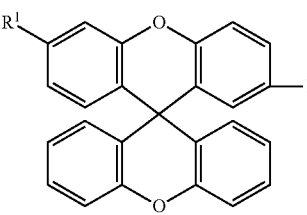

-continued formula (5j)
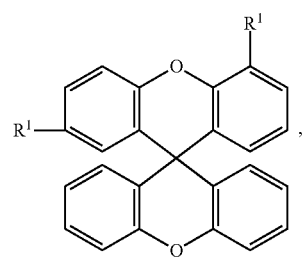

formula (5k)
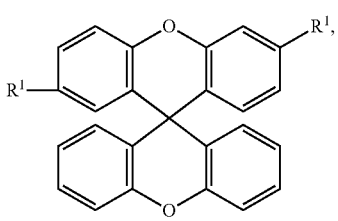

formula (5l)
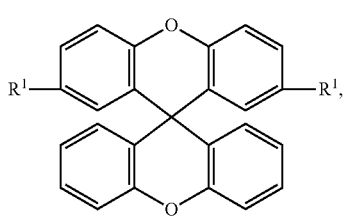

formula (5m)
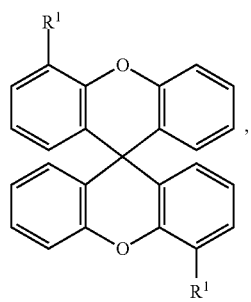

formula (5n)
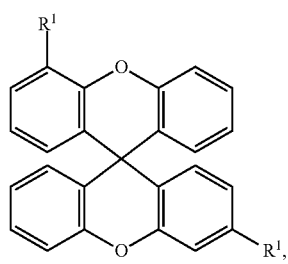

formula (5o)
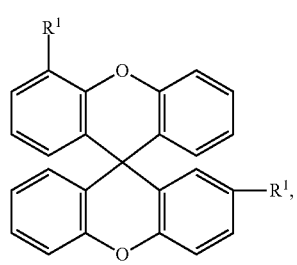

-continued formula (5p)
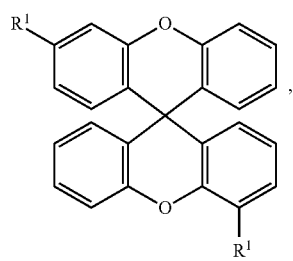

formula (5q)
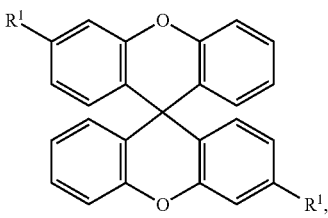

formula (5r)
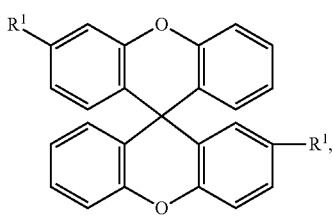

formula (5s)
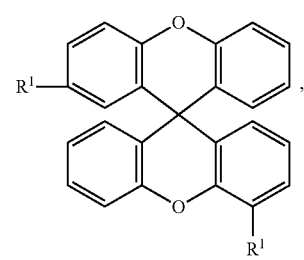

formula (5t)
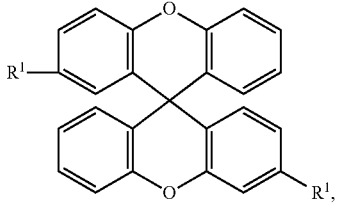

formula (5u)
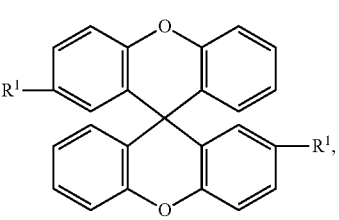

$R^1$ is selected on each occurrence, identically or differently, from the group consisting of H, D, F, Cl, Br, I, CN, $NO_2$, $N(Ar^1)_2$, $N(R^3)_2$, $C(=O)Ar^1$, $C(=O)R^3$, $P(=O)(Ar^1)_2$, $B(Ar^1)_2$, $Si(Ar^1)_3$, $Si(R^3)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which can be substituted by one or more radicals $R^3$, where one or more non-adjacent $CH_2$ groups can be replaced by $R^3C=CR^3$, $C\equiv C$, $Si(R^3)_2$, $C=O$, $C=S$, $C=NR^3$, $P(=O)(R^3)$, $SO$, $SO_2$, $NR^3$, $O$, $S$ or $CONR^3$ and where one or more H atoms can be replaced by D, F, Cl, Br, I, CN or $NO_2$, an aromatic or heteroaromatic ring system having 5 to 60 aromatic ring atoms, which can in each case be substituted by one or more radicals $R^3$, an aryloxy or heteroaryloxy group having 5 to 60 aromatic ring atoms, which can be substituted by one or more radicals $R^3$, where two or more adjacent substituents $R^1$ or $R^2$ can optionally form a monocyclic or polycyclic, aliphatic, aromatic or heteroaromatic ring system, which can be substituted by one or more radicals $R^3$;

$Ar^1$ is on each occurrence, identically or differently, an aromatic or heteroaromatic ring system having 5-30 aromatic ring atoms, which can be substituted by one or more non-aromatic radicals $R^3$; two radicals $Ar^1$ here which are bonded to the same N atom or P atom can also be bridged to one another by a single bond or a bridge selected from $N(R^3)$, $C(R^3)_2$, O or S;

$R^3$ is selected on each occurrence, identically or differently, from the group consisting of H, D, F, Cl, Br, I, CN, $NO_2$, $N(R^4)_2$, $C(=O)R^4$, $P(=O)(R^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which can be substituted by one or more radicals $R^4$, where one or more non-adjacent $CH_2$ groups can be replaced by $R^4C=CR^4$, $C\equiv C$, $Si(R^4)_2$, $C=O$, $C=S$, $C=NR^4$, $P(=O)(R^4)$, $SO$, $SO_2$, $NR^4$, $O$, $S$ or $CONR^4$ and where one or more H atoms can be replaced by D, F, Cl, Br, I, CN or $NO_2$, an aromatic or heteroaromatic ring system having 5 to 60 aromatic ring atoms, which can in each case be substituted by one or more radicals $R^4$, an aryloxy or heteroaryloxy group having 5 to 60 aromatic ring atoms, which ma be substituted by one or more radicals $R^4$, or a combination of these systems, where two or more adjacent substituents $R^3$ can optionally form a monocyclic or polycyclic, aliphatic ring system, which can be substituted by one or more radicals $R^4$;

$R^4$ is selected on each occurrence, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms can be replaced by D, F, Cl, Br, I or CN, where two or more adjacent substituents $R^4$ can form a mono- or polycyclic, aliphatic ring system with one another, with the proviso that for n=0, at least one substituent $R^1$ is present which is selected from the group consisting of CN, $N(Ar^1)_2$, $C(=O)Ar^1$, $P(=O)(Ar^1)_2$, $B(Ar^1)_3$, $Si(Ar^1)_3$, $Si(R^3)_3$ or an aromatic or heteroaromatic ring system having 5 to 60 aromatic ring atoms, which can in each case be substituted by one or more radicals $R^3$.

5. The compound according to claim 1, wherein the compound is substituted by at least one group $-C(=O)Ar^1$ or $-P(=O)(Ar^1)_2$ or an electron-deficient heteroaromatic ring system, where at least one substituent $R^1$ and/or $R^2$ or a monovalent group Ar is selected from structures of the formula (13) to (16) for $R^1$ or $R^2$ or the formulae (17), (18) or (19) for Ar,

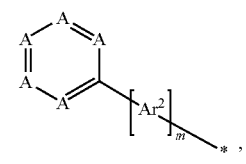

formula (13)

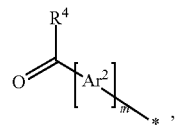

formula (14)

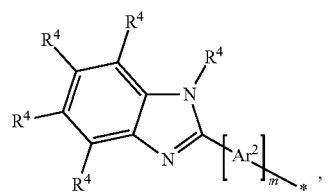

formula (15)

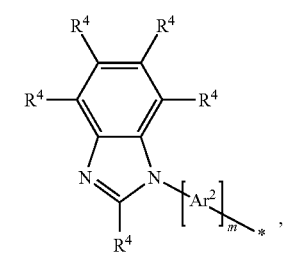

formula (16)

and/or at least one divalent or trivalent group Ar stands for a group of the formulae (17) to (19),

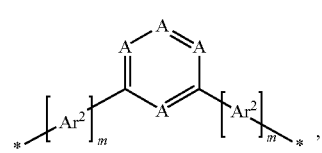

formula (17)

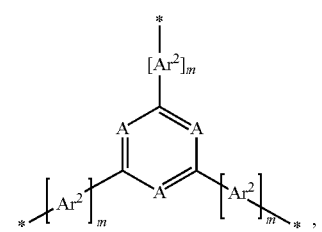

formula (18)

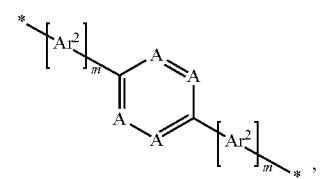

formula (19)

where $R^4$ and m have the meaning given in claim 1, * indicates the position of the bonding of the group of the formula (13) to (19) and furthermore:

A is on each occurrence, identically or differently, $CR^4$ or N, with the proviso that one, two or three groups A stand for N;

Ar² is, identically or differently on each occurrence, a divalent aromatic or heteroaromatic ring system having 5 to 16 C atoms, which can be substituted by one or more radicals R⁴.

6. The compound of claim 1, wherein the compound is substituted by at least one group which can be substituted by R³, or at least one substituent R¹ or R² stands for N(Ar¹)₂, where these groups are selected from group of the following formulae (35)-(49):

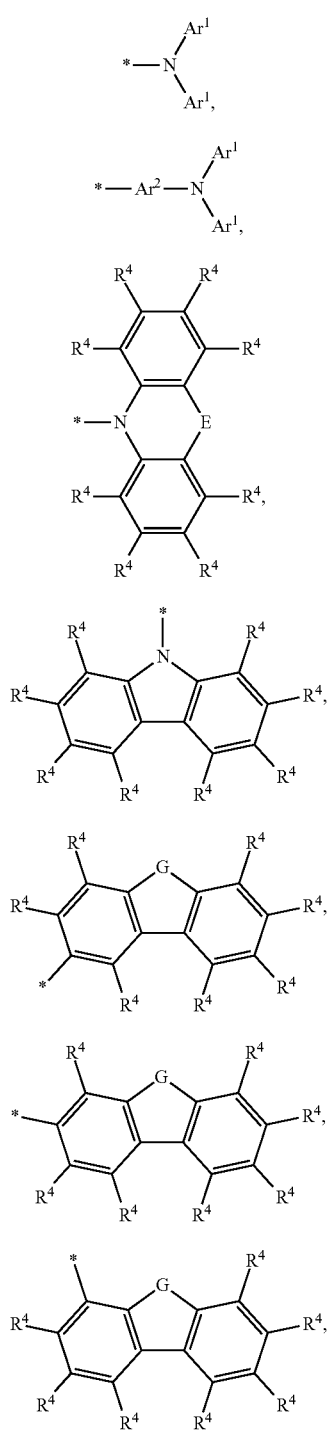

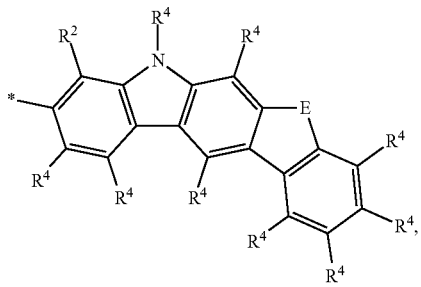

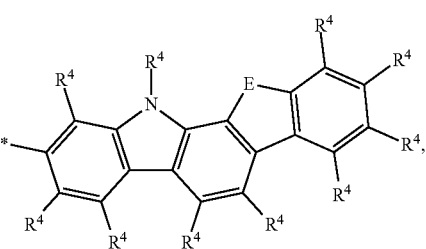

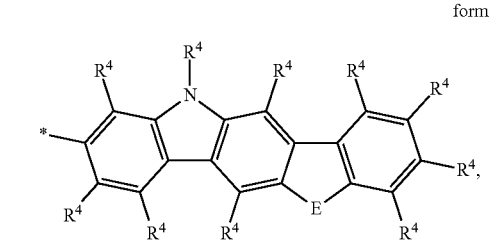

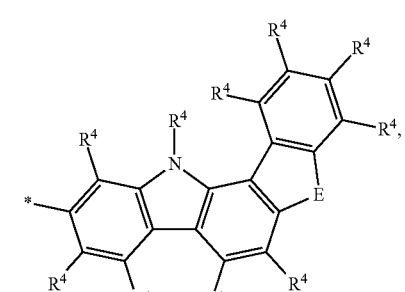

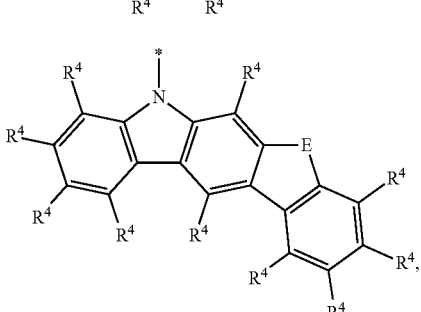

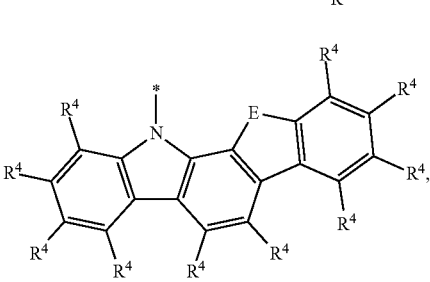

-continued

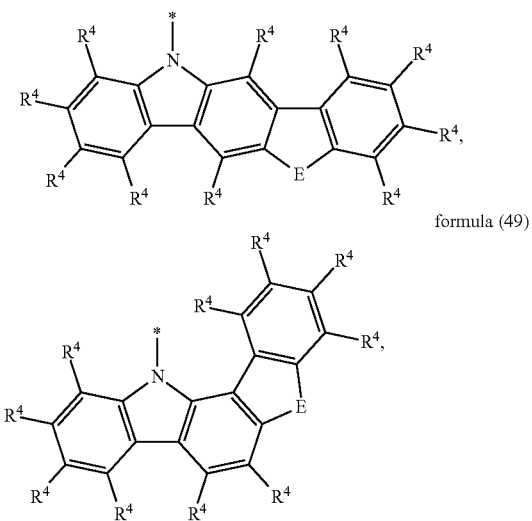

formula (48)

formula (49)

E is selected from the group consisting of $C(R^3)_2$, $NR^3$, O or S; and

G is selected from the group consisting of $NR^3$, O or S;

* indicates the position of the bonding of the group of the formulae (35) to (49), $Ar^2$ is, identically or differently on each occurrence, a divalent aromatic or heteroaromatic ring system having 5 to 16 C atoms, which can be substituted by one or more radicals $R^4$.

7. A process for the preparation of the compound according to claim 1, comprising the reaction steps of:
   a) synthesising a halogen-substituted spiro-9,9-bixanthene; and
   b) reacting the halogen-substituted spiro-9,9-bixanthene in a C—C coupling, C—N coupling, sililyation, phosphanylation, boranylation or polycondensation.

8. An oligomer, polymer or dendrimer containing one or more compounds according to claim 1, where one or more bonds from the compound to the polymer, oligomer or dendrimer are present instead of substituents at one or more positions.

9. An electronic device which comprises the compound according to claim 1.

10. The electronic device as claimed in claim 9, wherein the electronic device is selected from the group consisting of organic electroluminescent device, organic integrated circuit, organic field-effect transistor, organic thin-film transistor, organic light-emitting transistor, organic solar cell, dye-sensitised organic solar cell, organic optical detector, organic photoreceptor, organic field-quench device, light-emitting electrochemical cell, organic laser diode and organic plasmon emitting device.

11. An organic electroluminescent device which comprises the compound according to claim 1 as matrix material for fluorescent or phosphorescent emitters and/or as fluorescent emitter and/or in an electron-blocking or exciton-blocking layer and/or in a hole-transport layer and/or in a hole-injection layer and/or in a hole-blocking layer and/or in an electron-transport layer, depending on the precise substitution.

* * * * *